United States Patent [19]
Bylina et al.

[11] Patent Number: 5,914,245
[45] Date of Patent: Jun. 22, 1999

[54] SOLID PHASE ENZYME KINETICS SCREENING IN MICROCOLONIES

[75] Inventors: Edward J. Bylina, San Jose; William J. Coleman, Mountain View; Michael R. Dilworth, Santa Cruz; Christopher M. Silva, Sunnyvale; Mary M. Yang; Douglas C. Youvan, both of San Jose, all of Calif.

[73] Assignee: Kairos Scientific Inc., Santa Clara, Calif.

[21] Appl. No.: 09/098,202

[22] Filed: Jun. 16, 1998

Related U.S. Application Data

[60] Provisional application No. 60/082,440, Apr. 20, 1998.
[51] Int. Cl.[6] .............................. C12Q 1/44; C12Q 1/37; C12Q 1/54; C12Q 1/00
[52] U.S. Cl. ................................ 435/19; 435/23; 435/24; 435/14; 435/15; 435/25; 435/4; 435/808; 435/283.1; 435/968; 422/50
[58] Field of Search .................................. 435/19, 23, 24, 435/14, 15, 25, 4, 808, 283.1, 968; 422/50

[56] References Cited

PUBLICATIONS

Caldwell et al; "J. Microbiological Methods"; vol. 15(4); pp. 249–261; (1992) (Abstract).
Weaver et al; Methods (San Diego); vol. 2(3); pp. 234–247; (1991) (Abstract).

Primary Examiner—Louise N. Leary
Attorney, Agent, or Firm—Fish & Richardson P.C.

[57] ABSTRACT

A MicroColonyImager instrument and solid phase methods to screen cells expressing mutagenized enzymes for enhanced activity. The MicroColonyImager instrument and methods permit high throughput screening of enzyme libraries by time course analyses of single-pixels, using either absorption, fluorescence or FRET. This high throughput assay can detect small differences in enzyme rates within microcolonies grown at a nearly confluent density on an assay disk. Each microcolony is analyzed simultaneously at single-pixel resolution, requiring less than 100 ml substrate/measurement. By simultaneously assaying different substrates tagged with spectrally distinct chromogenic or fluorogenic reporters, the substrate specificity of an enzyme can be changed.

50 Claims, 7 Drawing Sheets

SOLID PHASE ENZYME KINETICS SCREENING IN MICROCOLONIES

This application claims the benefit of U.S. Provisional Application No. 60/082,440, filed Apr. 20, 1998.

STATEMENT AS TO FEDERALLY SPONSORED RESEARCH

This invention was made with Government support, awarded by the National Institutes of Health. The Government may have certain rights in the invention.

TECHNICAL FIELD

The invention relates generally to enzymes, and specifically to solid phase enzyme kinetics screening in microcolonies of biological cells.

BACKGROUND OF THE INVENTION

Research efforts in chiral chemistry and enantioselective production technologies continue to increase as the U.S. Food and Drug Administration and the European Committee for Proprietary Medicinal Products push pharmaceutical companies to market single-isomer drugs. Manufacturers are now required to characterize each enantiomer in all drugs that are proposed to be marketed as a mixture. The production of new racemates (mixtures of enantiomers) has ceased to be a viable commercial option with these new guidelines. The push to market chirally-pure drugs is being driven by the realization that often only one enantiomer of a racemate is responsible for efficacy, while the nonefficacious enantiomer has at best no physiological effect and at worst is responsible for adverse side effects. Thalidomide is a tragic example of a drug where efficacy resides in one enantiomer and the side effect, teratogenicity, resides in the other.

Among the enantioselective production technologies are kinetic resolution and asymmetric synthesis by biocatalysts, such as enzymes. Biocatalysis is becoming increasingly popular in drug and specialty chemical manufacturing, mainly due to its simplicity, versatility, and environmental acceptability. Among the more useful reactions by which chirality can be introduced are stereospecific hydrolysis and formation of ester and amide bonds, both of which reactions can be catalyzed by hydrolases. Of particular interest among the hydrolases are lipases, esterases, glycosidases, proteases, and amidases.

Many potential industrial applications for enzymes involve substrates, organic solvents and other reaction conditions that are never encountered in nature. Protein engineering can be used to change the properties of enzymes to supply the needs of pharmaceutical manufacturing. By carefully controlling in vitro mutation efficiencies and screening for enhanced catalytic properties over multiple generations, new enzymes can be developed that are hundreds of times more active than the natural enzymes in chemical process environments.

However, further exploration of this technology is severely limited by the current need to employ time-consuming liquid-phase assays for screening mutant libraries. Despite recent advances by pharmaceutical and biotechnology firms to accelerate their drug discovery efforts by developing automated liquid-phase screening systems, screening bottlenecks remain. For example, conventional 96-well microtiter plates, with 100–200 $\mu$l/well, are currently used in almost all screening. This volume results in less throughput than is desired.

Improvements in assay miniaturization would allow acceleration in the rate of screening, reduction in the cost per assay, and conservation of compounds that are either expensive or difficult to synthesize and purify. Thus, there exists in the art a need to develop a high throughput solid phase screening system, reducing effective assay volumes to 100 nanoliters (nl) or less.

In 1994, KAIROS Scientific Inc. developed and commercialized a PC-based ColonyImager capable of determining the absorption spectra of several hundred cell colonies on a single Petri dish (Youvan, Nature 369: 79–80, 1994). This device has proved very useful in the isolation of mutants of Rhodobacter capsulatus expressing natural pigments such as carotenoids and bacteriochlorophyll. In concert with directed evolution techniques, the ColonyImager was used to screen libraries of mutagenized photosynthetic bacteria for light-harvesting proteins that were undergoing directed evolution through repeated cycles of combinatorial mutagenesis. However, the throughput of the ColonyImager is limited to a few (~10) colonies per square centimeter.

Accordingly, the inventors have determined that it would be highly useful to automatically determine the spectroscopic characteristics, particularly over time, of a large number of cellular colonies expressing variants of a selected enzyme. The present invention provides a system and methods for accomplishing this end.

SUMMARY OF THE INVENTION

The present invention provides an instrument and methods for solid phase enzyme kinetics screening in microcolonies of biological cells. The invention shows that kinetics and spectral data can be accurately determined in microcolonies, and that microcolonies are amenable to single-pixel analyses for both kinetics and spectroscopy. The invention thus integrates automated spectrophotometric capabilities with high throughput screening of enzyme kinetics.

The invention provides an instrument for imaging and analyzing microcolonies of cells on a target. The instrument includes a light source for controllably emitting light having a selected set of wavelengths; a camera, for imaging light received from the target within a selected set of wavelengths; a sampling mechanism for selecting samples from the target; and a processor, coupled to the light source, the camera, and the sampling mechanism, for controlling the wavelengths of light emitted from the light source, the wavelengths of light imaged by the camera, and operation of the sampling mechanism. The instrument automatically images the target over time for changes in the optical signal of portions of the regions, and indicates which of the portions have a desired change over time in optical signal. The instrument can acquire kinetic as well as spectral data in several different modes, such as absorption, fluorescence, chemiluminescence, and fluorescence resonance energy transfer (FRET).

The invention also provides a method for imaging and analyzing microcolonies of cells. More than 100 optically distinct regions are formed on a substantially continuous base, with each region including at least one biological cell. The average density on the base is at least about 10 regions/$cm^2$. A chemical reaction is initiated in these regions that results in an optically detectable signal in the regions that changes over time. Each region is automatically optically monitored over time for changes in optical signal. The change over time in optical signal indicates which regions, and thus the cells in the region, have a desired characteristic.

The invention further provides a method of performing solid phase directed evolution enzyme screening. Gene expression is induced in a library of mutant cells on a solid phase, with the cells expressing variants of one or more selected enzymes. The average density on the base is at least about 10 regions/cm$^2$. The expressed variants are contacted with one or more optical signal substrates for the selected enzymes. Changes in the optical signal over time are detected in the microcolonies, with the changes over time indicating the enzymatic activity of the variants of the selected enzymes.

DESCRIPTION OF THE DRAWINGS

The file of this patent contains at least one drawing executed in color. Copies of this patent with color drawings will be provided by the Patent and Trademark office upon request and payment of the necessary fee.

Like numerals refer to like elements in the drawings.

DETAILED DESCRIPTION OF THE INVENTION

Figure 1:
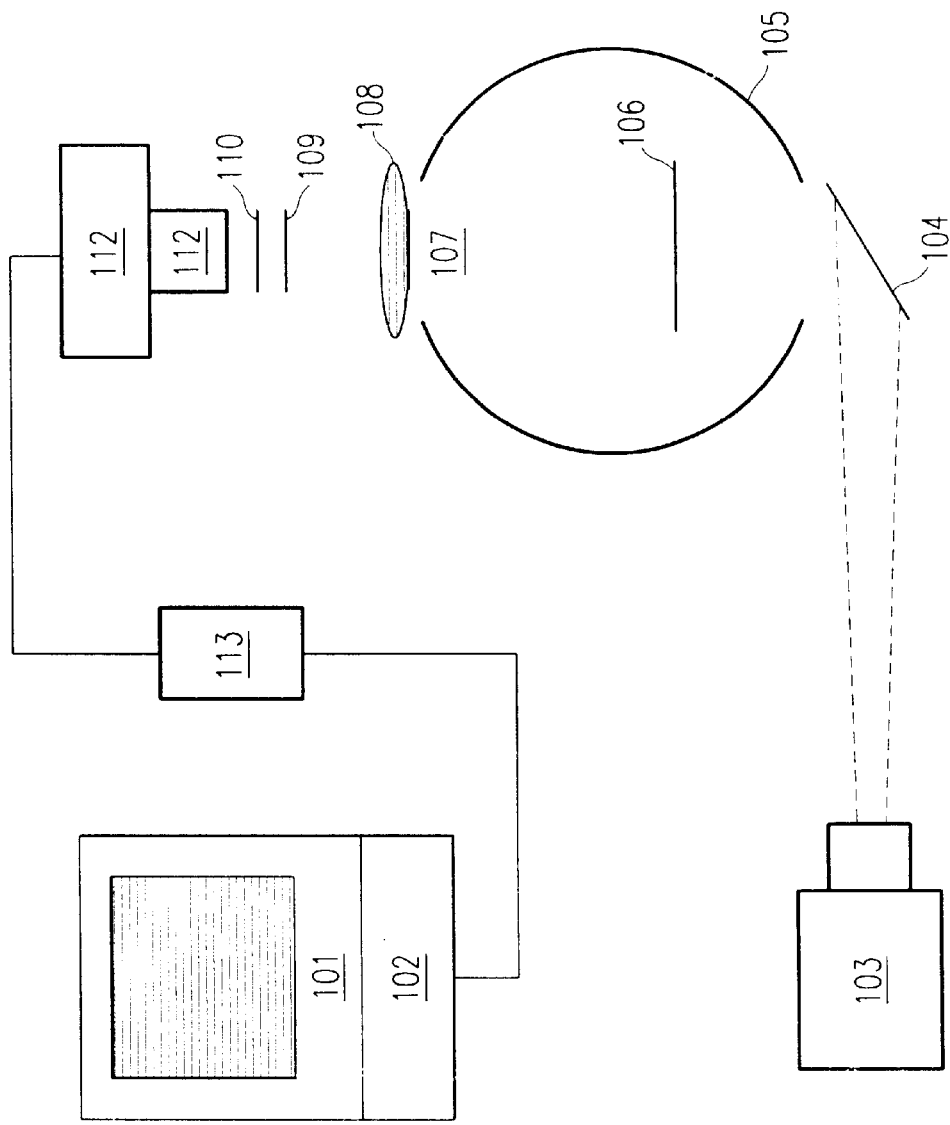
FIG. 1. is a depiction of the prototype MicroColonyImager (MCI).

The present invention provides an instrument and solid phase assays for high-throughput screening of libraries expressing mutagenized enzymes, for massively parallel screening of enzymes undergoing directed evolution, and for high-throughput screening of recombinant DNA libraries. The instrument is a new imaging spectrophotometer/fluorimeter, termed the MicroColonyImager (MCI). Use of the instrument and methods of the invention can lead to the isolation of variant enzymes having activities that are commercially useful for the organic/biochemical synthesis of various substances, including chiral pharmaceuticals.

Advances in chiral chemistry, enzymology and mutagenesis have made it feasible to evolve enzymes for a wide variety of chemical processes. The MicroColonyImager and directed evolution can be used in concert to provide custom evolution of enzymes for chiral chemistry by changing the substrate specificity, stereo specificity, region specificity of a reaction, rate of a reaction, thermostability, solvent stability, or other "screenable" properties of an enzyme. Use of the instrument and methods of the invention can also lead to the isolation of new enzyme activities that are useful in the synthesis, modification, or degradation of various substances.

Commercial opportunities for the use of the MicroColonyImager include the chiral drug market. As directed evolution techniques to improve enzymes (by enhancing their specificity, activity, or solvent and thermo-tolerance) are implemented for an increasing number of applications, such enzymes will have a greater impact on the global pharmaceuticals market.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present application, including definitions, will control. In addition, the materials, methods, and examples described herein are illustrative only and not intended to be limiting.

Other features and advantages of the invention will be apparent from the following detailed description, the drawings, and from the claims.

1. Instrument

The invention provides an instrument for imaging and analyzing microcolonies of cells on a target. The instrument includes a light source for controllably emitting light having a selected set of wavelengths; a camera for controllably imaging light received from the target within a selected set of wavelengths; a sampling mechanism for controllably selecting samples from the target; and a processor, coupled to the light source, the camera, and the sampling mechanism, for controlling the wavelengths of light emitted from the light source, the wavelengths of light imaged by the camera, and operation of the sampling mechanism. The instrument automatically images regions of the target over time for changes over time in an optical signal of portions of such regions, and indicates which of such portions have a desired change over time in optical signal.

A microcolony is a clump of cells that are clonally derived from a single parent cell. A microcolony differs from a colony, in that a colony is visible to the naked eye, where a microcolony need not be visible. A microcolony can be composed of any biological cells, including archaebacterial cells, bacterial or other prokaryotic cells, or eukaryotic cells, including plant, fungal, or animal cells.

Screening microcolonies has several advantages over screening colonies. Kinetics and spectral data are more accurately determined by using microcolonies rather than larger colonies. Microcolonies are amenable to single-pixel analyses for both kinetics and spectroscopy. Thus, indicating a "positive" microcolony is best done by pixel rather than by feature. In complex images such as confluent groups of microcolonies, feature extraction is inferior to single pixel analysis for identification of the "fastest" microcolonies because of edge effects and other artifacts.

Screening microcolonies also has several advantages over screening liquid samples. Because each microcolony and the small area of the disk surrounding it can be thought of as a biochemically distinct microreactor, the total amount of substrate supplied to the disk divided by the number of microcolonies gives the substrate volume per reactor. The 96-well microtiter plate technology for liquid phase assays requires a minimum of 50 μl/reaction well. By contrast, the MicroColonyImager has analyzed mutant enzyme libraries by using only 100–200 nanoliters (nl) substrate/reaction. This ratio is improved at least two-fold, using the improved instrument, simply by increasing the colony density. The use of fluorogenic substrates and new types of membranes decreases reaction volumes still further. This inherent advantage of the solid phase technique is extremely important for assays involving substrates that are expensive or difficult to synthesize.

Figure 2:
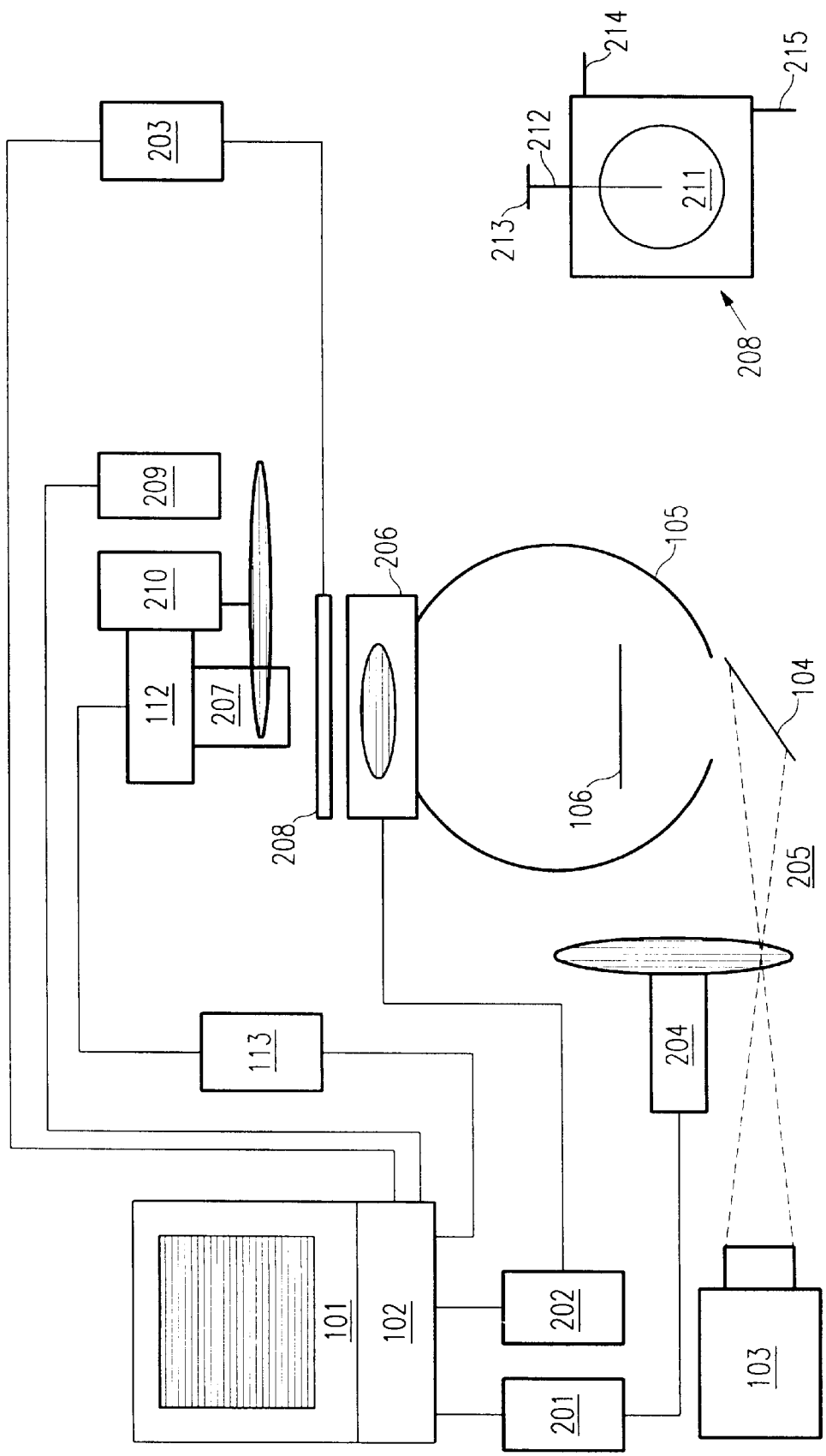
FIGS. 2. and 2A are a depiction of an improved MicroColonyImager.

A light source for controllably emitting light is shown in FIGS. 1 and 2 as element 103. The light source for controllably emitting light having a selected set of wavelengths can be any light source for which the set of wavelengths can be selected. Preferably, the light source is a monochromatic light source. Alternatively, the light source can provide a spectrum (i.e., multiple wavelengths) or white light.

Optionally, an integrating chamber interposed between the light source and the target for dispersing the emitted light to uniformly illuminate the target is also used to provide a consistent light source. An integrating chamber is shown in FIGS. 1 and 2 as element 105. The integrating chamber can be the integrating spheres and baffles used in the Colony-Imager and larger-format instruments, as described by Youvan et al. (*Methods Enzymol.* 246: 732–748, 1995), for targets ranging from Petri dish size (as in this instrument) to much larger devices with 250,000 $cm^2$ apertures. Other embodiments are described infra.

In another embodiment, light is directed from a fiber optic bundle coupled to a computer interfaced monochromator. The light bundle is directed in from above the target 108, without an integrating sphere 105. Flat field division by a "blank" image corrects for any deviations from uniform illumination. Thus the invention provides an instrument with a fiber optic illuminator.

A camera for controllably imaging light received from the target within a selected set of wavelengths is shown in FIGS. 1 and 2 as element 112. The camera can be any electronic camera that can be adapted to interact with the computer. For example, commercial cameras have been used in conjunction with the ColonyImager with megapixel-per-second digitizers (e.g., Photometrics model CH250). Preferably, the camera is a charge-coupled device (CCD) camera. The response of the CCD camera is linearly proportional to the light intensity, while for photographic film it is logarithmic. This makes the resolution in grey levels of the CCD higher than for ordinary film. The exposure time can be varied according to the light conditions. In the prototype MicroColonyImager, described infra, the cameras are LPT-interfaced CCD cameras that download small-format, binned images (100,000 pixels) in approximately 6 seconds, while requiring up to 60 seconds to download large-format, unbinned images (1.5 million pixels). These KAIROS K7 and K8 cameras are compatible with standard PC parallel ports. In the improved MicroColonyImager, described infra, the camera is a 4-megapixel K9 camera. By using newer technologies, e.g., the new IEEE 1494 or ethernet "FireWire", megapixel-per-second download rates in the K9 camera can be achieved while using the same 2K×2K Kodak CCD.

A sampling mechanism is shown in FIG. 2 as element 208. The sampling mechanism is used to differentiate different regions of the target. In one embodiment, the instrument automatically selects a sample with the sampling mechanism from at least one indicated portion. In the embodiment shown in FIG. 2, the sampling mechanism is a mechanical colony picker/marker 211. Micromanipulators of this type are sold by a number of robotics companies, for example, Zymark, Inc. (Hopkinton, Mass.). A simpler device can also be used. Several manufacturers, including Sutter Instrument Company (Novato, Calif.), sell stepper-motor controlled stages with various degrees of freedom. In FIG. 2, motors can move the stage in the x-dimension 214, y-dimension 215, and z-dimension 213. A preferred stage is a cost-effective stage with a clear aperture of at least 150 cm along both the x- and y-dimensions, with two additional degrees of freedom for picking/marking microcolonies. Specifications for positional accuracy are better than 75 microns in all dimensions, which is essentially single-pixel resolution, given the apparent target size projected to one CCD pixel. Highly accurate stages to vary the pathlength of femtosecond time-resolved spectrophotometers, which require stepping at 10-micron resolution, have been described by Bylina et al. (*Nature* 336: 182–184, 1988).

Alternatively, the sampling mechanism is a second, pin-registered "picking" station that is separate from the imaging spectrophotometer. This embodiment has the advantage of freeing the spectrophotometer for a second run, while the picking station is working on the previous assay disk.

The sampling mechanism can involve cost-effective hardware and software methods that do not rely on costly off-the-shelf robotics and can be used to indicate "positive" colonies. For example, it is possible to "drop" 3 mm grids bearing a 100 micron lattice (essentially transmission electron microscopy [TEM] grids) over "positive" colonies. A variety of grids are available, using different metals and grid patterns, from Energy Beam Sciences, Inc. (Agawam, Mass.). Imaging and stage software interact to confirm that the drop has occurred at the correct position by allowing the user to see the superimposed grid/target microcolony image before and after the drop. Low-tech methods, such as recovering the desired portion of the assay disk by hand with a Pasteur pipette, can then be used. This method (as opposed to well-defined robotics) reduces costs. Because of infrequent positive colonies, there should not be more than a few grids dropped per disk assay. This method also is amenable to moving the marked assay disk to a second station so that the region containing the desired microcolony can be retrieved under a dissecting scope. Recovery of the desired region of the assay disk by any of these sampling methods can then be coupled with plasmid transformation and rescreening to isolate a particular variant.

A processor is shown in FIGS. 1 and 2 as a computer 101 and LPT interface 102, with associated hardware elements. The processor is coupled to the light source, the camera, and the sampling mechanism, for controlling the wavelengths of light emitted from the light source, the wavelengths of light imaged by the camera, and operation of the sampling mechanism. Computer equipment for use in the instrument is commercially available. Controllers for the CCD camera, the temperature-controlled reaction chamber, the colony picker/marker, and filter wheels are also commercially available.

In a specific embodiment, the instrument includes a prototype MicroColonyImager, constructed to follow the time course of absorbance and fluorescence changes in the solid phase assay disk, as shown in FIG. 1. The prototype MicroColonyImager is constructed of a monitor 101, a computer with LPT interface 102, a monochromatic light source 103, a mirror 104, an integrating sphere 105, a baffle 106, a light exit port 107, a target 108, a longpass filter 109, lenses, including a +4 Diopter lens 110 and a 28 mm macro lens 111, a CCD camera 112, and a camera controller 113.

The integrating sphere 105, is optimal for illumination of the target 108 by using a well-engineered baffle 106 that effectively serves as an illumination background in either the fluorescence or absorption modes. This prototype MicroColonyImager differs significantly from the ColonyImager, described in the BACKGROUND, in that the working distance between the target 108 and the CCD lens 111 has been reduced from 70 cm to 10 cm and the number of pixels used has increased from 90,000 to 1.5 million. Along with changes in the relay optics, the prototype MicroColonyImager can image 8×6 cm targets 108 at 75 micron/pixel resolution. Given the inverse-square law for light intensity and the isotropic nature of fluorescence, the prototype MicroColonyImager thus achieves a 50-fold increase in fluorescence light-gathering ability over the ColonyImager. By combining a monochromatic illuminator 103, integrating sphere 105, close-up lens 110, longpass filter 109 and 1.5-megapixel CCD 75 micron resolution camera 112, single-pixel measurements were obtained across a 50 $cm^2$ target 108.

The prototype MicroColonyImager can analyze 15,000 individual pixels within a 1.5-megapixel image. Kinetic analysis of microcolonies imaged at single-pixel resolution has been demonstrated at a fixed observational wavelength in an absorbance mode, radiometrically calibrated for optical density. The prototype MicroColonyImager can also look at the full spectrum of single pixels at a fixed time point to acquire information on mixtures of chromogenic reporters.

In another specific embodiment, the invention includes an improved MicroColonyImager, as shown in FIG. 2. The improved MicroColonyImager further includes a filter wheel controller 201, a temperature controller 202, a stage controller 203, an illumination light source filter wheel and stepper 204, a temperature-controlled reaction chamber 206, relay optics 207, a stage 208, a filter wheel controller 209, an imaging optics filter wheel and stepper 210, a mechanical colony picker/marker 211, a rotation motor 212, a Z motor 213, an X motor 214, and a Y motor 215. The hardware is PC-based with parallel port 102 interfaces to at least five "black box" controllers for each of the major MicroColonyImager functionalities, including: illumination wavelength 201, imaging wavelength 209, sample temperature 202, CCD camera 113, and colony picking/marking 203.

Computer-interfaced filter wheels are added to the illumination light source filter wheel and stepper 204 and the imaging optics filter wheel and stepper 210. The controllers, stepper motors, and filter wheel assemblies can be customized devices purchased from Sutter Instruments (Novato, Calif.). For a number of engineering reasons, including factors related to illumination intensity, light gathering ability, and optical pupils, both the illumination light source filter wheel and stepper 204 and imaging optics filter wheel and stepper 210 use 1" diameter (discrete/Fabry Perot/all dielectric/10 nm FWHM) bandpass filters. Using a ganged system of 4 wheels in each assembly (10 positions, 9 filters and one clear aperture), 36 different wavelengths can be selected. This configuration provides 10 nm resolution over the visible and near-infrared.

Figure 3:
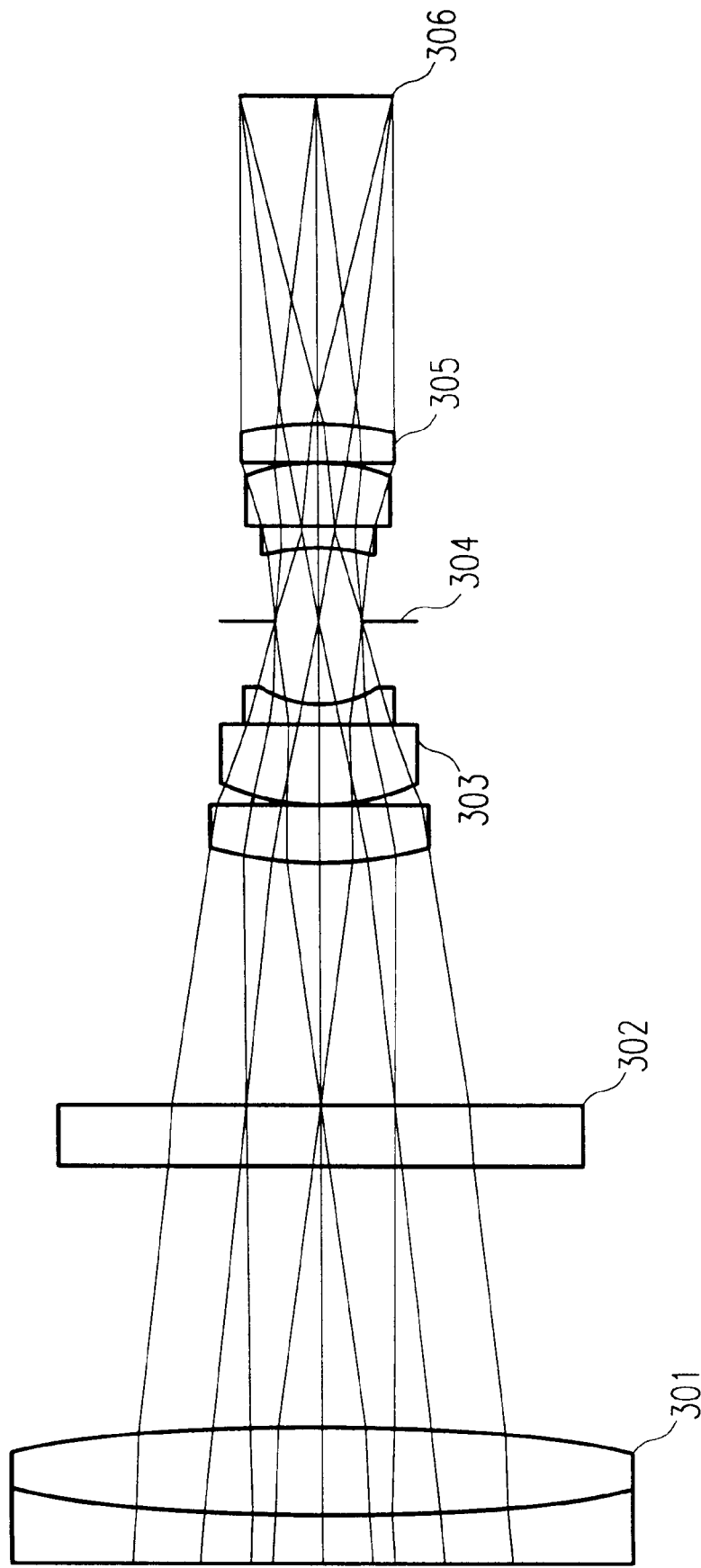
FIG. 3. is an expanded review of the MicroColonyImager relay optics (FIG. 2; item 207 using a ray-tracing simulation.

The relay optics 207 associated with the CCD camera 112 are sophisticated, to achieve image registration while maintaining low $f$-numbers and high light gathering abilities (see, FIG. 3). In FIG. 3, the elements are an objective lens 301; relay lenses 302, 303, and 305; filter position 304; and CCD image plane 306. This design was ray-traced with the Zemax program and was shown to be achromatic. This design also maintains image registration given the caveat that the interference filters have no more than 10 arc seconds of "wedge". The design of the relay optics and the objective lens (FIG. 2, 207; FIG. 3) for the CCD camera 112 takes into account the difficulty of combining a lens with a large pupil and light gathering ability (i.e., $f2.8$, 50 mm macro with +4 diopter close-up) with a means to selectively filter the light by wavelength and to maintain image registration. In this embodiment, discrete filters, rotated by an automated filter wheel 210, are used at a position in the relay optics 207 where the light is highly collimated (see, FIG. 3, position 304). Alternatively, a circular variable interference filter (CVIF) can be used, as shown by Youvan et al. (*Biotechnology* et alia<www.et-al.com>1: 1–16, 1997).

The physical size of the target assay disk 108 in the improved MicroColonyImager is 82 mm. By increasing the size of the disk from 47 to 82 mm, and roughly doubling the density of the colonies, ~50,000 microcolonies per assay disk can be analyzed.

An optically-clear, temperature-controlled reaction chamber 206 is installed in the MicroColonyImager to facilitate assays at controlled temperatures and in nonaqueous (organic) solvents. Thus, enzyme assays are performed under a range of conditions using solid phase materials that are imaged directly in real time. Minimization of the air space in the chamber above the imaged solid phase materials reduces evaporation during the course of the assay. Devices of this type are commercially available from Biological Optical Technologies (Butler, Pa.) and can be placed between the integrating sphere and the imaging optics.

The improved MicroColonyImager can analyze enzyme kinetic parameters from data based on absorbance, fluorescence excitation, or fluorescence emission for all of the pixels in a 4-megapixel image (i.e., single-pixel resolution). Additional functionality includes control and calibration software for either absorption, fluorescence emission, fluorescence excitation, or FRET. Each of these modalities has been radiometrically calibrated in other instruments, including High Resolution Imaging Microscope (HIRIM) for absorbance (see, *Biotechnology* et alia<www.et-al.com>4: 1–20, 1998) and *Fluorescence Imaging MicroSpectrophotometer* (FIMS) for fluorescence (Youvan et al., *Biotechnology* et alia<www.et-al.com>1: 1–16, 1997).

In one embodiment, the light source includes a variable filter for controlling the wavelengths of light emitted by the light source. Also in one embodiment, the camera includes a variable filter for controlling the wavelengths of light received by the camera. These features are depicted in FIG. 2 as an illumination light source filter wheel and stepper 204 and a imaging optics filter wheel and stepper 210, respectively.

2. Method for Imaging and Analyzing Microcolonies of Cells

The invention provides a method for imaging and analyzing microcolonies of cells. In excess of 100 regions are formed, each region including at least one biological cell on a substantially continuous base at an average density of at least about 10 regions/$cm^2$. A chemical reaction is initiated in such regions that results in an optically detectable signal that changes over time. Each region is automatically optically monitored over time for changes in the optical signal of portions of such regions. This indicates which of such portions have a desired change over time in optical signal.

A substantially continuous base can be any biologically acceptable substrate, such as a Petri dish, assay disk for growing bacteria, or an array of glass or plastic beads. In FIG. 1 and 2, the target 108 is a substantially continuous base. A substantially continuous base allows for free diffusion of liquid throughout its surface. In one embodiment, the average density of regions on the substantially continuous base is at least about 200 regions/cm$^2$. For example, in the 11-step method described infra, a bacterial library is deposited on 47 mm diameter assay disks to generate a density of 200–500 colonies/cm$^2$ and, the cells on the disks are then placed in contact with growth medium until microcolonies (~100 micron diameter) appear. By increasing the size of the disk from 47 to 82 mm, and roughly doubling the density of the colonies, ~50,000 microcolonies per disk can be analyzed. This increase in the size of the disks allows the processing of approximately 10$^6$ different clones within a relatively short time (1–2 days) using a single instrument. A library of this size provides enough complexity for a reasonably useful search of sequence space for a given functionality.

A selected enzyme can be any enzyme for which exists an optical signal substrate. For example the selected enzyme can be a hydrolytic enzyme, a protease, an esterase, a glycosidase, an isomerase, a lyase, a polymerase, a synthase, a synthetase, a transferase, or an oxido-reductase. An example of a hydrolytic enzyme is Agrobacterium β-galactosidase (abg), as described in EXAMPLE 1, or a restriction endonuclease, as described in EXAMPLE 8. Among the proteases with optical signal substrates are the serine proteases trypsin and chymotrypsin. An example of an esterase is Rhizopus lipase, as provided in EXAMPLE 7. Among the glycosidases are mannosidase, amyloglucosidase, cellulase, neuraminidase, β-galactosidase, β-glucosidase, β-glucuronidase, and α-amylase. Among the oxido-reductases are catalase, monooxygenase, dioxygenase, cytochrome oxidase, glucose oxidase, glutathione peroxidase, and monoamine oxidase. In another embodiment, a selected enzyme consists of a group of enzymes in an enzymatic pathway for which there exists an optical signal substrate. An example of this is the set of carotenoid synthesis enzymes described in EXAMPLE 9.

In one embodiment, the optical signal substrate can be a colored reactant or generate a colored product. The optical signal substrate can be a chromogenic substrate, fluorogenic substrate, chemiluminescent substrate, or fluorescence resonance energy transfer substrate. For example, the optical signal substrate can be an indolyl derivative, which is enzymatically cleaved in a colorimetric solid phase assay, as in the 11-step method of EXAMPLE 1. Hydrolytic cleavage of the glycosidic bond of the indolyl derivative at the 3-position generates the protonated (hydroxyl) form of indoxyl, which deprotonates and tautomerizes. In the presence of oxygen, two indoxyl molecules are then spontaneously oxidized and the C-2 carbon is deprotonated. The deprotonation causes the two indoxyl molecules to rapidly dimerize. The final product is an intensely colored indigo dye, which precipitates out of solution lysed or peeks not diffuse away from a lysed or permeabilized microcolony. This is important, since absorbance is monitored as a function of time in the solid phase assay.

TABLE 1

INDOLYL DERIVATIVES AND THE COLORS OF THEIR INDIGO PRODUCTS

| Indolyl Derivative | Indigo Product $\lambda_{max}$ (nm) |
| --- | --- |
| Red (6-chloro) | 540 |
| Magenta (5-bromo-6-chloro) | 565 |
| Iodo (5-iodo-) | 575 |
| X (5-bromo-4-chloro-) | 615 |
| Green (1-methyl-) | 665 |
| Y (unsubstituted) | 680 |

The sugar moiety can be replaced by other compounds to make the molecule a substrate for a variety of enzymes. For example, replacing the sugar with a carboxylic acid generates ester substrates for lipases and esterases.

The optical signal substrate can be a fluorogenic substrate. Fluorogenic substrates provide an important alternative to the indigogenic substrates used in the detection of product formation by absorbance. Among other things, they provide high sensitivity for improved detection; alternative "tags" to ensure that the mutant enzyme recognizes only the substrate itself; alternative spectral windows for multiplex imaging; and alternative detection modes.

Several glycosidic substrates for fluorescence assays are commercially available, and the chemistry of the fluorescent tags covers a wide range, including umbelliferone, fluorescein, and resorufin. Fluorescein and resorufin are also available as alkylated derivatives that form products that are relatively insoluble in water, a feature which is especially useful for solid phase assays. For example, fluorescence imaging can be performed using $C_{12}$-resorufin galactoside, produced by Molecular Probes (Eugene, Oreg.) as a substrate. In addition, other sugar derivatives are available that form insoluble fluorescent precipitates upon hydrolysis (TABLE 2). Enzymatic hydrolysis of these glycosides creates a highly fluorescent precipitate, the color of which is determined by the substituents on the 2-aryl ring. These types of substrates are readily adapted to the solid phase assay format of the MicroColonyImager.

TABLE 2

SUGAR DERIVATIVES THAT PRODUCE AN INSOLUBLE FLUORESCENT PRODUCT UPON HYDROLYSIS

| Sugar derivatives | Emission wavelengths of the products (using 375 nm excitation) |
| --- | --- |
| 2-(2-glycosyl-5-O-methyl)phenyl-4(3H)-quinazolinone | $\lambda_{em}$ = 450 nm |
| 2-(2-glycosyl-)phenyl-4(3H)-quinazolinone | $\lambda_{em}$ = 490 nm |
| 2-(2-glycosyl-4-O-methyl)phenyl-4(3H)-quinazolinone | $\lambda_{em}$ = 550 nm |

Fluorescence in a sample is measured using a fluorimeter. In general, excitation radiation, from an excitation source having a first wavelength, passes through excitation optics. The excitation optics cause the excitation radiation to excite the sample. In response, fluorescent compounds in the sample emit radiation which has a wavelength that is different from the excitation wavelength. Collection optics then collect the emission from the sample. Methods of performing assays on fluorescent materials are well known in the art and are described by Lakowicz (*Principles of Fluorescence Spectroscopy*, New York, Plenum Press, 1983) and Herman ("Resonance energy transfer microscopy," in: *Fluorescence Microscopy of Living Cells in Culture, Part B, Methods in Cell Biology*, vol. 30, ed. Taylor & Wang, San Diego, Academic Press, 1989, pp. 219–243).

The optical signal substrate can be a chemiluminescent substrate. Chemiluminescence is luminescence resulting from a chemical reaction, for example, the oxidation of luciferin in fireflies. Chemiluminescent substrates for several enzymes are available from Tropix (Bedford, Mass.). Among the enzymes are alkaline phosphatase, β-galactosidase, β-glucuronidase, and β-glucosidase.

The optical signal substrate can be a FRET substrate. FRET is a spectroscopic method that can monitor proximity and relative angular orientation of fluorophores.

A fluorescent indicator system that uses FRET to measure the concentration of a substrate or products includes two fluorescent moieties having emission and excitation spectra that render one a "donor" fluorescent moiety and the other an "acceptor" fluorescent moiety. The two fluorescent moieties are chosen such that the excitation spectrum of the acceptor fluorescent moiety overlaps with the emission spectrum of the excited moiety (the donor fluorescent moiety). The donor moiety is excited by light of appropriate intensity within the excitation spectrum of the donor moiety and emits the absorbed energy as fluorescent light. When the acceptor fluorescent protein moiety is positioned to quench the donor moiety in the excited state, the fluorescence energy is transferred to the acceptor moiety, which can emit a second fluorescent light. The emission spectra of the donor and acceptor moieties have minimal overlap so that the two emissions can be distinguished. Thus, when acceptor emits fluorescence at longer wavelength than the donor, then the net steady state effect is that the donor's emission is quenched, and the acceptor now emits when excited at the donor's absorption maximum. Alternatively, the FRET acceptor can be a molecule that accepts fluorescence energy from the donor molecule and dissipates the energy without emitting fluorescence.

The efficiency of FRET depends on the separation distance and the orientation of the donor and acceptor fluorescent moieties. An extremely useful feature of this effect is that the transfer efficiency generally depends on $r^{-6}$, where r is the separation distance between the fluorophores. Thus, even a small increase in the separation distance abolishes the FRET signal. FRET can be manifested as a reduction in the intensity of the fluorescence emission from the donor moiety, reduction in the lifetime of the excited state of the donor moiety, or emission of fluorescent light at the longer wavelengths (lower energies) characteristic of the acceptor moiety when the sample is excited at a wavelength that is optimal for the donor. When an enzyme cleaves a FRET substrate, the fluorescent moieties physically separate and FRET is decreased accordingly. Tables of spectral overlap integrals are readily available (e.g., Beriman, *Energy transfer parameters of aromatic compounds*, Academic Press, New York and London, 1973).

The amount of substrate or product in a sample can be determined by measuring the amount of FRET in the sample. The amount of FRET can be determined by any spectral or fluorescence lifetime characteristic of the excited donor moiety. Changes in substrate concentration can be determined by monitoring FRET over time after the sample and the fluorescent indicator have been brought into contact. Changes in the amount of FRET can then be measured. Intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored. High fluorescence quantum yield of the acceptor moiety is desirable if the emission from the acceptor moiety is to be monitored to determine substrate concentration in a sample.

Changes in the amount of FRET can be determined as a function of the change in the ratio of the amount of fluorescence from the donor and acceptor moieties. Changes in the absolute amount of indicator, changes in excitation intensity, and changes in turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

FRET has been incorporated into a number of enzyme assays. For restriction enzymes, double-labeled fluorogenic oligonucleotides have been used to assay restriction cleavage activity. Short duplex oligomers with fluorescein and rhodamine attached to the opposing 5'-termini have already been employed as substrates in microscopic imaging by Uchiyama et al. (*J. Biol. Chem.* 271: 380–384, 1996) and in solution assays to determine Michaelis parameters by Ghosh et al. (*Nucleic Acids Res.* 22: 3155–3159, 1994). Protein fusions containing BFP and GFP linked together have already been employed as substrates in protease assays by Mitra et al. (*Gene* 173: 13–17, 1996).

The optical signal substrate can also be a substrate that does not require a separate "tag" in order to be chromogenic, fluorogenic, or lumigenic. For example, many enzymes involved in the biosynthesis of natural products (e.g., pigments) convert colorless molecules into colored, fluorescent, or luminescent ones by directly modifying the chemical structure of untagged substrates. Alternatively, the enzymes may convert colored substrates into colorless ones. Thus, the kinetics of color production (or destruction) can be used to monitor the activity of the enzyme with respect to its untagged substrate. The color reaction is initiated either by adding an exogenous untagged substrate, or, if the substrate is an endogenous metabolite, by inducing expression of the enzyme. A particular chemical modification (e.g., hydroxylation) can be introduced at different locations on a given substrate molecule by using different variants of the same enzyme or by altering the solvent composition. This difference in regiospecificity of the enzyme can be used to create differently colored products.

The method can further include the step of measuring essential enzymatic parameters for the variants of the selected enzyme expressed by such DNA. Among the enzymatic parameters are $K_m$, $k_{cat}$, substrate specificity, and enantiomeric excess (ee). Other enzymatic parameters include the stereo specificity and regiospecificity of a reaction. Values of $K_m$ and $k_{cat}$ are calculated by standard kinetic methods used in the enzymological arts.

(a) $K_m$ is the Michaelis constant, for the chemical reaction in which substrate (S) is converted to product (P), by an enzyme (E). Enzymes associate with substrates to form an enzyme-substrate complex (ES). $K_m$ is an apparent dissociation constant, and is related to the enzyme's affinity for the substrate; it is the product of all the dissociation and equilibrium constants prior to the first irreversible step in the pathway. Often it is a close measure of the ES dissociation constant. In the simplest model (the Michaelis-Menten model), E and S associate with a rate constant $k_1$, while ES dissociates back to E and S with a constant $k_{-1}$, or forms E and P with a constant $k_2$ (the turnover number). The Michaelis-Menten analysis incorporates the additional assumption that $k_2$ is much less than $k_{-2}$. In this formulation, $K_M=(k_2+k_{-1})/k_1$. $K_M$ can also be derived for more complex enzyme kinetics (for a full account, see Fersht, *Enzyme Structure and Mechanism*, 2nd ed., W. H. Freeman and Co., New York, 1988, pp. 98–101)

(b) $k_{cat}$ is the catalytic constant, a first-order rate constant corresponding to the slowest step or steps in the overall catalytic pathway. $k_{cat}$ represents the maximum number of molecules of substrate which can be converted into product per enzyme molecule per unit time (which only happens if the enzyme is "saturated" with substrate), and thus is often known as the turnover number. In the Michaelis-Menten model, $k_{cat}=k_2$.

(c) Substrate specificity is the ability of an enzyme to recognize and specifically bind a substrate. Substrate specificity is a function of protein structure. High or strict substrate specificity indicates the ability to bind and convert only one or a limited number of substrates. An enzyme with a broad substrate specificity converts a wide range of related substrates.

(d) Enantiomeric Excess. Optical purity is the ratio of the observed optical rotation of a sample consisting of a mixture of enantiomers to the optical rotation of one pure enantiomer. For a mixture of (+)- and (−)-enantiomers, with composition given as the mole or weight fractions F(+) and F(−) (where F(+)+F(−)=1), the enantiomer excess is defined as |F(+)−F(−)|. Frequently this term is abbreviated as "ee". Enantiomeric excess can be used as a yardstick to measure the relative substrate specificity of a given enzyme, under conditions where the two competing substrates are enantiomers of each other.

In one embodiment, the method further includes the step of obtaining a sample of an indicated microcolony. The DNA obtained from the samples is transformed into biological cells. Methods of obtaining DNA from samples and transforming the DNA into biological cells are well known in the art (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991; Bauer et al.,*J. Biol. Chem.* 271: 23749–23755, 1996).

In EXAMPLE 1, a Beckman DU 7400 diode array spectrophotometer equipped with a Peltier temperature-controlled/ motor-driven 6-cell holder was used for measuring in vitro enzyme kinetics. The Beckman software package includes analysis software for enzyme kinetics (Michaelis-Menten, Lineweaver-Burk, Eadie-Hofstee and Hanes-Wolf plots, as well as Hill plots and inhibitor plots). For fluorescence measurements, a Photon Technology International QM-1 spectrofluorimeter, which also has software for kinetic analyses, was used.

In one embodiment, the step of automatically optically monitoring each region further includes the step of imaging the regions with a camera. The camera forms a pixel image of the regions and each region spans at least one pixel. As described supra, microcolonies are amenable to single-pixel analyses for both kinetics and spectroscopy. Thus, an advantage of the MicroColonyImager is the ability to acquire spectral data on microcolonies.

Figure 4:
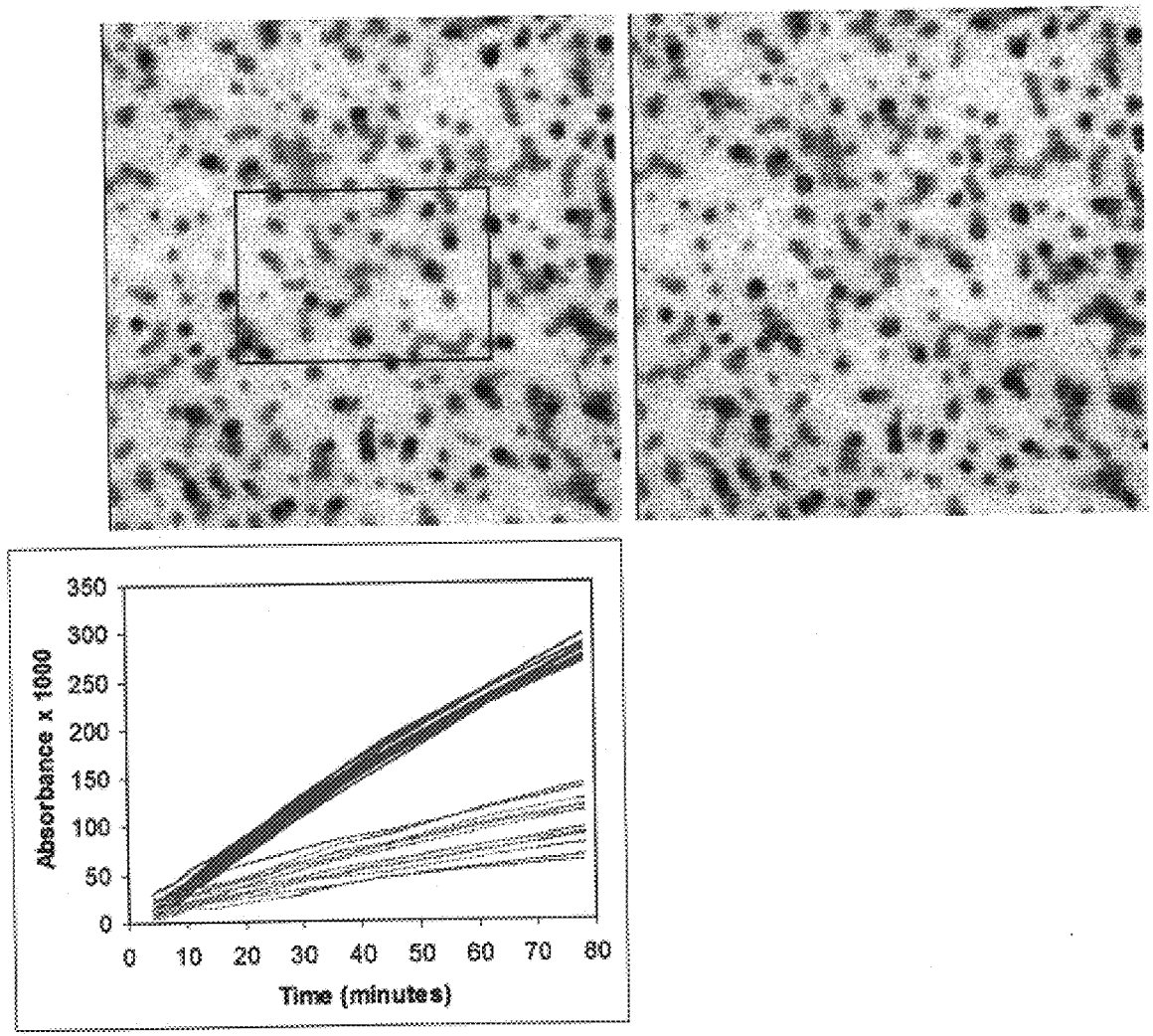
FIG. 4 shows the single-pixel kinetics of a mixture of microcolonies, each microcolony expressing one of two mutants of Agrobacterium β-glucosidase (abg), Y380F and R377T.

To differentiate between two classes of mutants whose activities differ by a relatively small amount, it is useful to acquire and sort single-pixel data, rather than feature data (where an example of the latter might be averages of grayscale values from pixels deemed to fall within one object). The reason can be understood by considering two types of colonies plated at high density on a filter surface: one has fast kinetics and one has slower turnover. As the size of each microcolony increases until it approaches the apparent size of each pixel at the target plane, edge pixels from the "faster" (more chromogenic) colonies appear to be similar in grayscale value (or optical density) to the center pixels of lighter colonies displaying slower enzyme kinetics, because edge pixels combine information from both the colony and background. Thus, the processed data from the colonies create a single feature, where the value reported for the merged colonies is intermediate between the two actual values. However, if every microcolony is sufficiently large to fully cover at least one pixel, acquiring and sorting single-pixel data is the most certain method of identifying the most chromogenic pixels on the assay disk (for example, see the pixels from the "faster" mutant, as depicted in FIG. 4). Edge pixels also reduce the apparent intensity of a fluorescence feature and should be eliminated, similarly. This innovation is rather simple but extremely powerful for machine vision and automatically indicating microcolonies.

In one embodiment, the step of indicating includes the step of color-coding an image of the regions to indicate which of such portions have a desired change over time in optical signal. In the 11-step method described infra, the prototype MicroColonyImager is prepared for a kinetics run by setting the parameters to be suitable for a given calorimetric indicator. For example, the instrument is set to 615 nm in absorption mode for the chromogenic substrate 5-bromo-4-chloro-3-indolyl-β-D-galactoside (X-gal). For experiments involving multiple substrates, at least two wavelengths are selected. In the improved MicroColonyImager, two filter wheels are used to select the wavelength, the illumination light source filter wheel and stepper 204 and the imaging optics filter wheel and stepper 210.

In one embodiment, the method of the invention further includes the step of recovering samples from the portions having the desired change over time in optical signal. A mechanical colony picker/marker 211 for automatically recovering samples from the portions of the target having the desired change over time in optical signal is depicted in FIG. 2.

In another embodiment, the enzyme of interest or recombinant DNA library is encoded by a virus, so that infection by the virus results in the expression of the enzyme of interest or recombinant DNA library encoded by the virus. In one specific embodiment, the virus is a lytic virus, such as the lytic bacteriophage λ. In another specific embodiment, the virus is a temperate virus, such as a temperate bacteriophage. Thus, bacteriophage plaques within a lawn of bacteria on a target can be used instead of microcolonies of biological cells on a target. Cells infected with phage are mixed with uninfected bacteria, added to liquefied agar, and poured onto the surface of a solid support (such as a petri dish). As the bacteria grow to form a bacterial lawn, infected cells release virus particles that infect adjacent cells in the bacterial lawn. When the plate is grown, the solid support will contain confluent growth of cells containing regions where cell growth is slowed (or cells are lysed) due to infection by the phage particle. Additionally, a library of mutant bacteriophage (instead of mutant plasmids) can express variants of selected enzymes. High densities of plaques on the plate are generated. When a lytic bacteriophage is used to infect the cells, lysis of the cells is accomplished by the phage itself. Optical signal substrates can be brought in contact with the plaques. Bacteriophage are recovered from positive plaques on the solid support and bacteriophage or bacteriophage DNA reintroduced into cells by methods well-known in the art (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991).

3. Methods of Performing Solid Phase Directed Evolution Enzyme and Biodiversity Screening The invention provides a method of performing solid phase directed evolution enzyme screening. Gene expression is induced in a library of mutant cells on a solid phase, each cell expressing a variant of a selected enzyme or group of enzymes in an enzymatic pathway, to generate a density of at least 10 microcolonies of cells/cm$^2$. The contents of the cells are contacted with an optical signal substrate specific for the selected enzyme or group of enzymes in an enzymatic pathway for which there exists an optical signal substrate. Changes over time are detected in an optical signal generated by the optical signal substrate in the microcolonies, because the changes over time indicate enzymatic activity of the variants.

In one embodiment, changes over time are detected in any optical signal generated by the optical signal substrate in the microcolonies. The microcolonies that display higher rate of change in such optical signal are indicated, because the higher change over time indicates enhanced enzymatic activity of the variants of the selected enzyme in the corresponding microcolonies.

In one embodiment, a library of mutant cells expressing variants of a selected enzyme to generate a density of at least 10 microcolonies of cells/cm$^2$ is grown on a solid phase. Gene expression is induced in the cells. The cells are lysed. An optical signal substrate specific for the selected enzyme is applied to the lysed cells. Changes over time are detected in an optical signal generated by the optical signal substrate in the microcolonies. Those microcolonies that display greater changes over time in such optical signal are indicated, wherein the greater changes over time indicate enhanced enzymatic activity of the variants of the selected enzyme in the corresponding microcolonies.

In another embodiment, the invention provides a method of performing enzyme discovery screening from biodiversity. In this embodiment, the library of cells used to generate microcolonies consists of cells containing a recombinant DNA library constructed from genomic DNA isolated from individual organisms, mixed groups of organisms, or genomic DNA extracted directly from the environment. A recombinant DNA library can also be constructed from double-stranded cDNA that is generated from mRNA. Methods for construction of recombinant DNA libraries are well known in the art (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991; Robertson et al., *Soc. Indust. Microbiol. News* 46: 3–7, 1996; Short, *Nature Biotechnology* 15: 1322–1323, 1997) and both premade and custom libraries are commercially available [e.g., from Stratagene (La Jolla, Calif.)]. Methods for isolation of genomic DNA used in the construction of recombinant DNA libraries are well known in the art (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991; Zhou et al., *Appl. Environ. Microbiol.* 62: 316–322, 1996; Robertson et al., *Soc. Indust. Microbiol. News* 46: 3–7, 1996; Short, *Nature Biotechnology* 15: 1322–1323, 1997). Microcolonies are generated at a density of at least 10 microcolonies of cells/cm$^2$. The contents of the cells are contacted with an optical signal substrate specific for the desired enzymatic activity. Changes over time are detected in an optical signal generated by the optical signal substrate in the microcolonies, because the changes over time indicate the desired enzymatic activity.

Exposure of the expressed variants can be accomplished by lysing or permeabilizing the cells. In one embodiment, the cells are lysed. The cells can be lysed by any of several methods known to those of skill in the art, including by enzymes, heat shock, ultrasound, and the use of organic solvents (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991; Bauer et al., *J. Biol. Chem.* 271: 23749–23755, 1996; Beliveau et al., *J. Bacteriol.* 173: 5619–5623, 1991; Lo et al., *Biochem. Cell Biol.* 64: 73–76, 1986; Koenen et al., *EMBO J.* 1: 509–512, 1982). In the 11-step method, the assay disk is transferred to a "lysis chamber" where it is covered with a thin film of aqueous buffer and exposed briefly to chloroform vapor.

In another embodiment, the cells are permeabilized, rather than lysed. The cells can be permeabilized by any of several methods known to those of skill in the art, such as by enzymes (see, Sambrook et al., *Molecular Cloning: A Laboratory Manual*, Cold Spring Harbor Laboratory, Cold Spring Harbor, N.Y., 1989; Ausubel et al., eds. *Current Protocols in Molecular Biology*, Wiley Interscience, N.Y., 1991).

In one embodiment, error-prone mutagenesis of DNA encoding a selected enzyme is performed. The DNA is transformed into biological cells to make a library of mutant cells expressing variants of the selected enzyme. The library of mutant cells is grown on a solid phase to generate a density of at least 10 microcolonies of cells/cm$^2$. Gene expression is induced in the cells. The cells are lysed or permeabilized. An optical signal substrate specific for the selected enzyme is applied to the lysed cells. The microcolonies are imaged over time to detect changes over time in an optical signal generated by the optical signal substrate. Those imaged microcolonies that display optimal changes over time in such optical signals are indicated, wherein the optimal changes over time indicate the desired enzymatic activity of the variants of the selected enzyme in the corresponding microcolonies.

An enzyme is typically much more active when catalyzing the reaction for which it has been selected in nature than it is when catalyzing the same reaction in an industrial process. However, evolving industrial biocatalysts with novel specificities or tolerances from naturally occurring enzymes requires an efficient mutagenesis strategy in order to be practical. The evolution of a new, useful enzyme requires an effective strategy for accumulating many such small improvements. The instrument and method of the invention ensure that small enhancements brought about mainly by single mutations can be measured.

Beneficial mutations can be accumulated by rational design, sequential generations of random mutagenesis and screening, or (random) recombination. Among the techniques that can be used to obtain mutations include error-prone PCR; DNA shuffling; site-directed mutagenesis; cassette/cartridge mutagenesis; chemical mutagenesis; mutator strain induced mutagenesis (for specific details, see, Sambrook et al., *Molecular Cloning: A Laboratory Manual*, Cold Spring Harbor Laboratory, Cold Spring Harbor, N.Y.; 1989; Ausubel et al., eds. *Current Protocols in Molecular Biology*, Wiley Interscience, N.Y., 1991). Several advanced techniques for the generation of modified enzymes have been described:

(a) Rational Design. Methods of rational design, using a variety of site-directed mutagenesis procedures, are well known in the art (see, Sambrook et al., *Molecular Cloning: A Laboratory Manual*, Cold Spring Harbor Laboratory, Cold Spring Harbor, N.Y., 1989; Ausubel et al, eds. *Current Protocols in Molecular Biology*, Wiley Interscience, N.Y., 1991).

(b) Recursive Ensemble Mutagenesis. A generally applicable combinatorial method, termed recursive ensemble mutagenesis (REM) (Arkin & Youvan, *Bio/Technology* 10: 297–300, 1992; Arkin & Youvan, *Proc. Natl. Acad. Sci. U.S.A* 89: 7811–7815, 1992), finds functional proteins that are many mutational steps from wild type. Many of the iterative steps normally performed by a digital computer are embodied in this molecular genetics technique. An algorithm for protein engineering was developed to produce diverse populations of phenotypically related mutants whose members differ in amino acid sequence. This method uses a feedback mechanism to control successive rounds of combinatorial cassette mutagenesis. Starting from partially randomized "wild-type" DNA sequences, a highly parallel search of sequence space for peptides fitting an experimenter's criteria is performed. Each iteration uses information gained from the previous rounds to search the space more efficiently. Small groups of residues are randomized in parallel to identify, at each altered position, amino acids which lead to functional proteins. By using optimized nucleotide mixtures deduced from the sequences selected from the random libraries, proteins with simultaneously altered sites are derived. Recursive ensemble mutagenesis is advantageous where many residues must be changed simultaneously to achieve a specific engineering goal (Delagrave & Youvan, *Bio/Technology* 11: 1548–1552, 1993; Delagrave et al., *Protein Eng.* 8: 237–242, 1995).

(c) DNA shuffling. DNA shuffling is a powerful process for directed evolution, which generates diversity by recombination, combining useful mutations from individual genes. A polymerase chain reaction (PCR)-based method of DNA shuffling has been described by Stemmer (*Proc. Natl. Acad. Sci. U.S.A.* 91: 10747–10751, 1994). Libraries of chimeric genes are generated by random fragmentation of a pool of related genes (e.g., by DNase I digestion and purification of small random fragments), followed by reassembly of the fragments in a self-priming PCR. Template switching causes crossovers in areas of sequence homology, resulting in in vitro recombination. Oligonucleotides with 3' and 5' ends that are homologous to the gene can be added to the fragment mixture and incorporated into the reassembled gene, so that mixtures of synthetic oligonucleotides and PCR fragments can be mixed into a chimeric gene at defined positions based on homology. Thus, single and multigene traits that require many mutations for improved phenotypes can be evolved rapidly.

(d) Sequential Random Mutagenesis. Sequential random mutagenesis, as described by Moore & Arnold, is a rapid and inexpensive method for the evolution of proteins (Moore & Arnold, *Nature Biotechnology* 14: 458–467, 1996; Moore & Arnold, *Adv. Biochem. Eng.* 58: 1–14, 1997; Kuchner & Arnold, *Trends Biotechnol.* 15: 523–530, 1997). The sequential random mutagenesis method is effective for many protein engineering problems and has received great attention from industry. This method requires no X-ray structure, very little DNA sequencing, and only a few days of manipulation for each mutagenic cycle. This simple approach is based on arguments regarding the low predicted yield of beneficial mutations and the severe search constraints imposed by screening. The number of possible different amino acid sequences one can introduce into any given enzyme is so vast that an exploration of their functions must be carefully guided in order to avoid becoming hopelessly lost. When error-prone PCR is performed on the gene of interest, a library of altered enzyme genes is created that contains relatively few (single or double) amino acid substitutions in each member of the library. Screening the reaction products of these mutagenized gene libraries identifies any variants showing enhanced activity. Although the progeny in these mutagenized gene libraries generally resemble their parents, new features can develop as mutations accumulate, such that the descendants can be quite different from their ancestor. Therefore, directed evolution of new, useful enzymes also relies on having an effective strategy for accumulating many such small improvements. The sequential random mutagenesis method involves performing sequential rounds of random mutagenesis to create a mutant library, coupled with screening of the resulting enzyme variants. In each generation a single variant is chosen to parent the next generation, and sequential cycles allow the evolution of the desired features.

The methods described supra are not exclusive. Methods for in vitro gene recombination, such as Stemmer's "DNA shuffling," can be used to combine individual beneficial point mutations identified during one or more generations of mutagenesis/screening. The effect of combining beneficial point mutations usually appears to be additive, further improving the function of the resulting enzyme. This method is also useful for removing deleterious mutations that accumulate during the cycles of random mutagenesis by backcrossing the evolved enzyme gene with the original enzyme gene.

The random mutagenesis strategies outlined above are especially useful for improving preexisting activities in an enzyme catalyst. However, error-prone PCR techniques are not adequate for hard problems in which individual mutations are not by themselves beneficial, but are favorable only in the context of one or more other mutations. Multiple amino acid substitutions may be required, for example, in order for an enzyme to accept a substrate that is significantly different from its natural substrate. Heuristic rules, based on structural data and the physicochemical properties of enzyme and substrates, must be incorporated into these types of mutagenesis schemes. In this situation, one needs to be able to screen much larger, more complex libraries, containing two or more amino acid substitutions, in order to develop the desired activities. The increased screening capacity of the MicroColonyImager makes it much easier to identify useful mutants in these high-complexity libraries.

In a specific embodiment, the method provides a new solid phase enzyme screening technique to facilitate the directed evolution of enzymes. A concise presentation of the preferred embodiment of this method follows. This 11-step method begins with the gene encoding an enzyme and concludes with the isolation of an "evolved" enzyme with improved properties under selection. While this method is described for an absorption mode and chromogenic substrates, the method can also use enzyme model systems using fluorogenic and FRET substrates.

1. Error-prone PCR is used to randomly mutagenize the enzyme-encoding DNA. The DNA is transformed into *E. coli* to make a library of mutants expressing enzyme variants.
2. The library is deposited on 47 mm diameter assay disks to generate a density of 200–500 colonies/cm$^2$ and the cells on the disks are grown on agar plates until microcolonies (~100 micron diameter) appear.
3. The assay disk (with colony side up) is transferred to an induction plate containing IPTG and grown at 30° C. for 4–5 hours (~200 micron diameter).
4. The assay disk is transferred to a "lysis chamber" where it is covered with a thin film of aqueous buffer and exposed briefly to chloroform vapor.
5. The MicroColonyImager is prepared for a kinetics run by setting software and hardware parameters so that they are suitable for a given calorimetric indicator. The instrument is set to 615 nm in absorption mode for X-gal.
6. The assay disk bearing microcolonies is transferred to the MicroColonyImager sample/reaction compartment, which contains a paper wick. The wick ensures that the membrane is uniformly bathed in a chromogenic substrate at saturating concentrations. Approximately 0.5–1 ml of substrate is added (at 1 mg/ml for galactosides or glucosides).

7. The disk is imaged at set time intervals for approximately one hour (or until the microcolony color is fully developed to the endpoint).

8. The MicroColonyImager highlights microcolonies that display the highest absorbance, while insuring that the change in absorbance with respect to time is linear, indicative of an initial enzyme velocity. In multiple substrate experiments, spectroscopic data are acquired for the different chromogenic substrates.

9. The desired portion of the assay disk (at the position of a "positive" microcolony) is recovered by hand with Pasteur pipettes. The disk portion is transferred to a tube containing a buffered solution and the DNA obtained is retransformed.

10. Positive colonies are separately grown and analyzed in vitro, so that the essential enzymatic parameters such as $K_m$, $k_{cat}$, substrate specificity, and enantiomeric excess (ee) can be determined.

11. Based on measured improvement in such factors, one variant is picked, and steps 1–10are repeated for each cycle of directed evolution in the random sequential mutagenesis method until a mutant enzyme with the desired characteristics is obtained.

The following examples are intended to illustrate but not limit the invention. While they are typical of those that might be used, other procedures known to those skilled in the art may alternatively be used.

EXAMPLE 1 abg As a Model System; abg Mutants Differentiated

This EXAMPLE shows the feasibility of the method of the invention, using the model enzyme system Agrobacterium β-glucosidase (abg). Abg is an enzyme from *Agrobacterium faecalis* that hydrolyzes β-glucosides. In this EXAMPLE, abg mutants differing by only 3-fold in $k_{cat}$ were differentiated. In addition, error-prone mutagenesis was used to change the substrate specificity of the enzyme from glucoside to galactoside.

The catalytic mechanism of the wild-type Abg protein and several active site variants has been studied in detail. Abg is non-specific, catalyzing the hydrolysis of substituted glucosides, galactosides, xylosides, fucosides, and arabinosides. Given the versatility of this enzyme, abg is an ideal candidate for directed evolution experiments.

Abg mutants were obtained from Professor Anthony Warren at the University of British Columbia.

In this EXAMPLE, abg activity was screened using hydrolysis of an indolyl derivative in a colorimetric assay. For measuring in vitro enzyme kinetics, a Beckman DU 7400 diode array spectrophotometer equipped with a Peltier temperature-controlled/motor-driven 6-cell holder was used, using p-nitrophenyl-glucoside (PNP-glucoside) as the substrate.

The prototype MicroColonyImager was used to acquire enzyme kinetics data. FIG. 4 shows a randomly distributed mixture of *E. coli* microcolonies expressing one of two abg variants (approximately 10% Y380F and 90% R377T). The mutant enzymes differ in $k_{cat}$ for the chromogenic substrate, 5-bromo-4-chloro-3-indolyl-β-D-galactoside (X-gal). Data from 15 pixels having the highest rate of increase in absorbance are plotted in red in FIG. 4, lower left panel, along with data from pixels on 15 "slow" colonies. These form two discrete groups, differing by roughly 3-fold in velocity. The 150 "fastest" pixels (1% of the green box, upper left panel) were mapped onto the upper right panel to highlight the faster kinetics of the Y380F mutants.

Mutants Y380F and R377T which have 42% and 16% activity, respectively, compared to wild-type abg were used in this EXAMPLE. The Y380F variant of abg contains a phenylalanine (Phe) substitution for the tyrosine (Tyr) at position 380, while the R377T variant of abg contains a threonine (Thr) substitution for the arginine (Arg) at position 377. The Y380F variant is about 3× more active than the R377T enzyme, as measured by an in vitro assay. X-gal was used instead of 5-bromo-4-chloro-3-indolyl-β-D-glucoside (X-glu) due to the greater solubility of X-gal. The region-of-interest shown in FIG. 4, from the 47 mm assay disk, is 150×100 pixels (15,000 pixels). This is 1% of the capacity of the K8 CCD, or only 0.3% of the 4-megapixel K9 CCD. The kinetic plot shows that the MicroColonyImager software automatically identified the 15 fastest pixels in the region of interest (ROI); these were color-coded red and mapped onto the image. Kinetics for these "fast" pixels were plotted (red) in the bottom panel and compared to manually-selected center pixels from less chromogenic colonies (gray). Two separable populations of pixels are clearly identified by this procedure, and their measured activities reflect the known kinetic difference between Y380F and R377T (i.e., 3-fold). Not only are the initial velocities linear with time, but the measured distribution of velocities matches the 10:90 mix.

This EXAMPLE shows that the method is very robust in picking the centers of "fast" colonies, which differ by less than three-fold in turnover number from other colonies.

EXAMPLE 2 abg as a Model System; the Substrate Specificity Changed from Glucoside to Galactoside An advantage of the MicroColonyImager is its ability to acquire spectral data on microcolonies. In this EXAMPLE, error-prone mutagenesis was used to change the substrate stereo specificity of abg from glucoside to galactoside using a two-color tagging system. Red-gal (6-chloro-3-indolyl-β-D-galactoside) and X-glu (5-bromo-4-chloro-3-indolyl-β-D-glucoside), whose indigo products absorb at 540 nm and 615 nm, respectively, were used as substrates.

The Y380F pseudo-wild-type abg enzyme is a better glucosidase than galactosidase; hence, the Y380F pseudo-wild-type abg enzyme cleaves X-glu more efficiently than Red-gal. Exposing these abg-containing cells to a 50:50 Red-gal+X-glu solution generates bluish colonies. Following error-prone mutagenesis, however, any abg microcolony mutants that favor the galactoside over its epimer (glucoside) should appear redder than the pseudo-wild-type in the solid phase assay.

To test the imaging system with a "mock" sample, pure β-galactosidase was used to cleave various defined mixtures of Red-gal and X-gal. Red-gal was pre-mixed with X-gal in the following percentage ratios, respectively: (A) 100:0; (B) 90:10; (c) 70:30; (D) 50:50; (E) 30:70; (F) 10:90; (G) 0:100. Each of these mixtures was completely hydrolyzed by adding 1 unit of *E. coli* β-galactosidase. The indigo products of each reaction were then spotted onto an assay disk for imaging. This assay disk was then imaged with the MicroColonyImager, and the absorption spectrum was measured for each spot. As expected, the resultant indigo products shift from red to blue as the X-gal/Red-gal ratio is increased.

To confirm in vivo that different indigo products generated by known enzymes with different substrate specificities could be distinguished, an assay disk containing microcolonies of cells expressing either E. coli β-galactosidase alone or a GFP-abg (Y380F) fusion protein was treated with a solution containing ~1 mg/ml (total) of Red-gal and X-glu. The MicroColonyImager was able to distinguish microcolonies containing β-galactosidase (red in color) from those microcolonies containing abg (blue in color). The correct identification of the colonies was confirmed by the presence of the GFP marker (i.e., green fluorescence) in those colonies that turned blue, and by the absence of the marker in those colonies that turned red.

By using the 11-step solid phase assay outlined supra and the prototype MicroColonyImager, the substrate specificity of abg was changed from a preference for glucoside substrates to a preference for galactoside substrates after one cycle of error-prone PCR.

PCR primers were designed to amplify an AvrII-SalI fragment containing the final two-thirds of the abg gene with the Y380F mutation (these restriction sites were unique in the expression plasmid). The PCR reactions were "poisoned" with increasing amounts of $MnCl_2$, to decrease the fidelity of DNA polymerase and introduce mutations into the amplified fragment. After restriction and gel purification, the mutagenized fragments were ligated into the expression vector and transformed into E. coli. This mutagenized library of abg genes was deposited on 47 mm diameter/0.2 $\mu$m pore size polycarbonate membrane disks (Poretics Products), produced by Osmonics (Livermore, Cailf.). The disks were transferred to LB plates containing kanamycin and isopropyl thio-62 -D-galactoseide (IPTG), and the plates were incubated at 30° C. until microcolonies appeared. The disk was then transferred to a pre-wetted paper wick in a large glass Petri dish. The wetted filter was exposed to chloroform vapor for 60 seconds, which caused the cells in the microcolonies to lyse. The microcolony-bearing disk (~10,000 microcolonies) was then transferred to a second paper wick (Whatman 114 paper) wetted with 1000 $\mu$l of a solution containing ~1 mg/ml of both Red-gal and X-glu and then imaged with the MicroColonyImager. One microcolony on the disk was found to display a strong preference for the Red-gal substrate, while several other microcolonies showed increased reactivity on Red-gal relative to X-glu compared to the starting abg enzyme. Data from the screen capture of the prototype MicroColonyImager user interface is shown in FIG. 4, 5, and 6.

Figure 5:
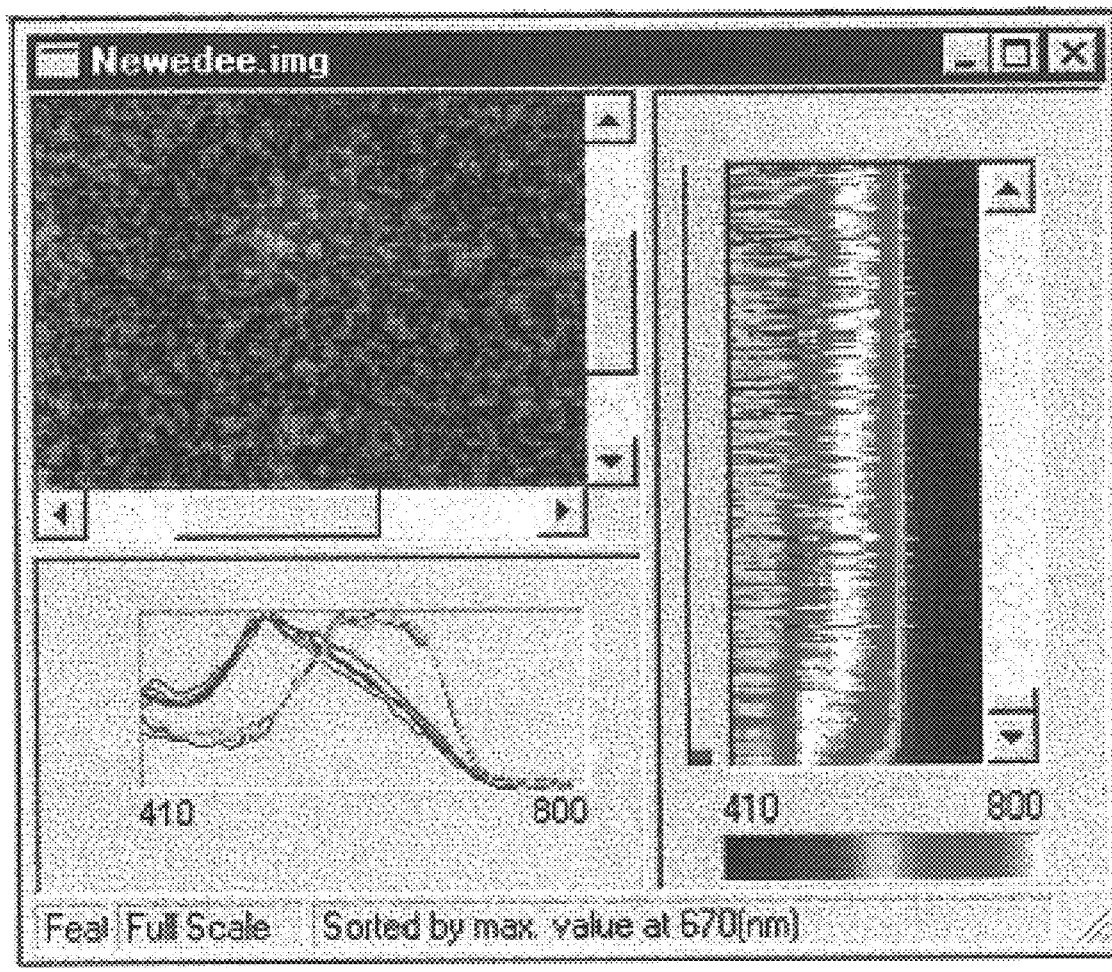
FIG. 5 is a solid phase assay disk bearing~10,000 colonies expressing abg after error-prone mutagenesis. It shows one colony in this small region-of-interest (upper left window) in which the glucosidase activity has been converted to predominantly galactosidase activity (color-coded red). The spectral plots (absorbance versus wavelength) are shown in the lower left plot window.
Figure 6:
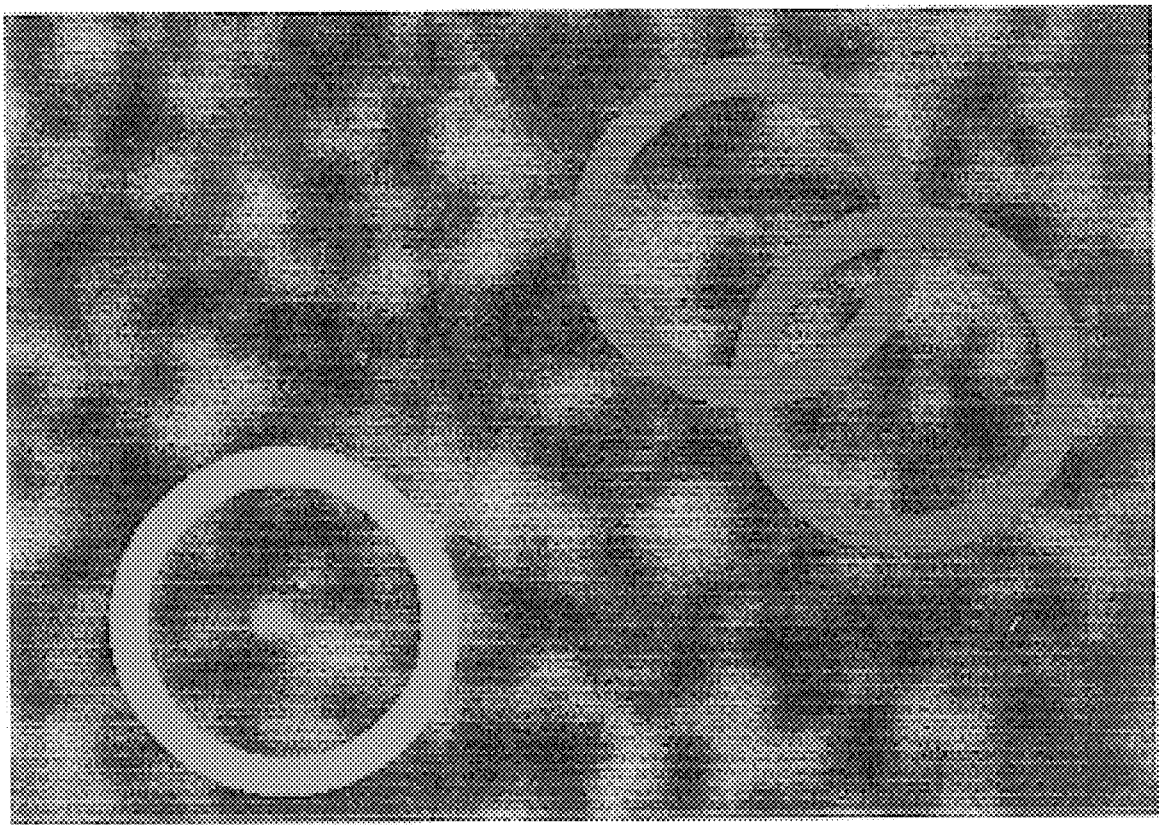
FIG. 6 is an enlargement of a portion of the image window from FIG. 5 showing "Red-gal preferring" pixels overlaid by the MicroColonyImager on the microcolony. Two extreme "X-glu preferring" pixels are also indicated by green overlays.

FIG. 5 is a solid phase assay disk bearing ~10,000 colonies expressing abg after error-prone mutagenesis. FIG. 5 shows one colony in this small region-of-interest (upper left window) in which the glucosidase activity has been converted to predominantly galactosidase activity (color-coded red). The spectral plots (absorbance versus wavelength) in the lower left plot window show the spectra of extreme pixels absorbing maximally at 540 nm where the substrate 6-chloro-3-indoylyl-β-D-galactoside ("Red-gal") is preferentially cleaved as opposed to extreme pixels absorbing maximally at 615 nm where the substrate 5-bromo-4-chloro-3-indolyl-β-D-glucoside ("X-glu") is preferentially cleaved. The "Red-gal preferring" pixels have been sorted to the bottom of the contour plot (right window) and the actual spectra that are plotted are indicated by color-coded tic marks to the extreme lower left of the contour plot. Only 1/60th of the color contour plot is displayed for this region-of-interest (15,000 pixels or rows). FIG. 6 is an enlargement of a portion of the image window from FIG. 5 showing "Red-gal preferring" pixels overlaid by the MicroColonyImager on the microcolony in which the glucosidase activity has been converted to predominantly β-galactosidase activity. Two extreme "X-glu preferring" pixels are also indicated by green overlays. For clarity, these MicroColonyImager-generated images were retouched to add the large colored circles.

After the abg variant with a preference for the galactoside substrate was identified, a tiny portion of the disk containing the "positive" microcolony was recovered by hand with a Pasteur pipette. DNA was eluted and used to electroporate E. coli. The resulting transformants were re-assayed to identify the desired abg variant and to purify it away from any other variants that may have been carried over during picking.

A second solid phase assay of these transforrnants showed that >50% of the transformants had a preference for Red-gal.

Thus, the stereo specificity of Agrobacterium β-glucosidase was shifted from a preference for glucoside to a preference for galactoside using error-prone PCR mutagenesis. In this EXAMPLE, identifying potentially useful mutants required only one cycle of error-prone PCR, after which the candidate mutants were found at a frequency of approximately 1 in 10,000.

EXAMPLE 3

Evolving abg for Enhanced Thermostability

Many potential industrial users of enzymes are interested in employing biocatalysts only if these can be easily integrated into existing chemical processing streams. Since this often involves high temperature environments, it is useful to provide for engineering thermostability (and possibly thermoactivity) into a candidate enzyme of mesophilic origin, as described by Lasa & Berenguer (*Microbiologia* 9: 77–89, 1993) and Cowan (*Essays Biochem.* 29: 193–207, 1995). There is also a potential bonus, in that increased thermostability often imparts increased resistance to chemical agents such as detergents and organic solvents. Lopez-Camacho et al. have demonstrated that random mutagenesis can be used to improve the thermostability of a bacterial β-glucosidase expressed in E. coli (Lopez-Camacho et al., *Biochem. J.* 314: 833–838, 1996).

The MicroColonyImager is used to engineer temperature stability into abg, by isolating mutant abg whose properties are enhanced at various temperatures, as compared to the wild type enzymes. The Y380F pseudo-wild type abg is evolved to catalyze efficient hydrolysis of glycoside substrates at elevated temperatures by using the 11-step method and gradually increasing the reaction temperature following successive rounds of random mutagenesis and recombination. The reaction temperature is controlled in the improved MicroColonyImager by a temperature-controlled reaction chamber (see, FIG. 2, item 206).

EXAMPLE 4

Evolving abg for Catalysis in Organic Solvents

Industrial applications of biocatalysts sometimes require enzymes that can function in an unnatural solvent environment. Many substrates for commercially important enzyme reactions are soluble only in non-aqueous media, and many commercially important enzymes likewise show enhanced stereoselectivity in certain organic solvents. There is also much recent interest in using organic solvents to control aspects of oligosaccharide synthesis by glycosidases.

The MicroColonyImager is used to engineer solvent stability into abg, by isolating mutant abg whose properties are enhanced in media with organic solvents, as compared to the wild type enzymes. The Y380F pseudo-wild type abg is evolved to catalyze efficient hydrolysis of glycoside substrates in various solvents by using the 11-step method and gradually increasing the organic solvent concentration following successive rounds of random mutagenesis and recombination. The reaction is controlled in the improved MicroColonyImager by a sealed temperature-controlled reaction chamber which minimizes evaporation of the solvent (see, FIG. 2, item 206). Incorporating this capability into the MicroColonyImager involves relatively minor adjustments, such as selecting microcolony disks with the appropriate chemical resistance, and optionally adjusting the detection system for any solvent-dependent spectral shifts.

EXAMPLE 5

Using GFP Fusions to Facilitate Downstream Analyses of Potential Mutants

Usually, pools of potentially useful bacterial mutants are analyzed by growing up small aliquots of each mutant clone and rupturing the cells in a French press. The enzyme activity of each of these crude lysates can then be analyzed spectrophotometrically by adding a small volume of the crude lysate to a solution of an optical signal substrate, e.g., p-nitrophenyl derivatized substrate, which releases the bright yellow p-nitrophenol, or PNP, upon hydrolysis. This technique cannot provide information on the specific activity ($k_{cat}$), however, because the protein concentration of the enzyme of interest is not known. Knowledge of the specific activity is important because apparent increases in velocity could simply be the result of increased synthesis of the protein (i.e., promoter-up mutations). Since there are a multitude of proteins in the lysate, the mutagenized enzyme must first be purified before a measurement of $k_{cat}$ can be made. For a candidate pool of many potential mutants, this is a laborious and time-consuming process.

To streamline this process for abg, an abg-GFP chimera was constructed as a starting template for abg mutagenesis. The green fluorescent protein (GFP), which forms an internal fluorophore autocatalytically, emits fluorescence at approximately 510 nm (for a review, see Misteli & Spector, *Nature Biotechnology* 15: 961–964, 1997). The green fluorescent proteins of cnidarians, which act as their energy-transfer acceptors in bioluminescence, are suitable fluorescent proteins for use as fluorescent indicators. A green fluorescent protein (GFP) is a protein that emits green light, and a blue fluorescent protein (BFP) is a protein that emits blue light. GFP has been isolated from the Pacific Northwest jellyfish, *Aequorea victoria*, the sea pansy, *Renilla reniformis*, and *Phialidium gregarium*. A variety of Aequorea-related GFPs having useful excitation and emission spectra have been engineered by modifying the amino acid sequence of a naturally occurring GFP from *Aequorea victoria* (see, Prasher, *Gene,* 111: 229–233, 1992; Heim, et al., *Proc. Natl. Acad. Sci., USA,* 91: 12501–04, 1994; Delagrave et al., *Bio/Technology* 13: 151–154, 1995; Lossau et al., *Chem. Physics* 213: 1–16, 1996). Mutagenesis studies have produced GFP mutants with shifted wavelengths of excitation or emission (see, Heim & Tsien, *Current Biol.* 6: 178–182, 1996).

The cDNA of GFP can be concatenated with those encoding many other proteins by recombinant genetic techniques; the resulting fusions often are fluorescent and retain the biochemical features of the partner proteins (see, Cubitt, et al., *Trends Biochem. Sci.* 20: 448–455, 1995). GFP has been fused to a number of different proteins to provide an intracellular marker.

In order to validate the solid phase screening technique against standard protocols, a $His_6$-GFP-tag was added to the abg structural gene by the method of Mitra et al. (*Gene,* 173: 13–17, 1996). Although their use is not essential for evolving enzymes with the MicroColonyImager, green fluorescent protein (GFP) tags are very helpful for determining enzyme concentration in crude lysates, a feature that facilitates high throughput screening for improved $k_{cat}$. The upstream histidine-rich region allows afffinity purification by $Ni^{2+}$resin chromatography, since the six histidine residues bind nickel ions. Thus, the presence of the $His_6$-GFP-tag facilitates rapid purification and quantitation of the mutagenized proteins. The chimeric gene expressed a protein with, from the N-terminus, a $His_6$-tag region of 20 amino acids, a GFP region of 238 amino acids, a linker region of 25 amino acids, and an abg region of 459 amino acids. Transcription is initiated from a T7 promoter, which is IPTG inducible. The $His_6$-GFP-abg fusion protein was purified and assayed spectrophotometrically (using p-nitrophenyl glucoside) to show that these tags did not change the $k_{cat}$ or $K_m$ of variants as previously described. For fluorescence measurements, a Photon Technology International QM-1 spectrofluorimeter, which has software for kinetic analyses, was used.

Crude lysate from cells expressing the GFP(RS8)/Y380F fusion protein was diluted over an 8-fold range to simulate potential prep-to-prep variation in yield. β-glucosidase activity ($V_{max}$) was measured spectrophotometrically at 37° C. and pH 6.8 using p-nitrophenyl-glucoside as the substrate. Fluorescence from the GFP tag was measured using 470 mm excitation and 508 mm emission, which is appropriate for the GFP(RS8) variant. The fluorescence counts were simultaneously measured for a set of dilutions of a purified standard of GFP(RS8)/Y380F, whose protein concentration is known. The response was linear. Normalizing the crude lysate fluorescence by the fluorescence of the standard thus enables the calculation of the specific activity ($k_{cat}$) of a given fusion protein in the lysate. By dividing the activity of an unknown mutant lysate by its level of GFP fluorescence and then normalizing those fluorescence counts to an abg-GFP chimera standard whose protein concentration is already known, the specific activity of the enzyme in the lysate can quickly be calculated, without needing to first purify the enzyme.

EXAMPLE 6

Engineering abg to Catalyze Efficient Hydrolysis or Synthesis of Unusual Glycosides Since mutants have been isolated that show enhanced activity on substrates containing D-galactose (the C-4 epimer of D-glucose), more exotic substrates, such as ones containing D-mannose (the C-2 epimer of D-glucose), L-idose (the C-5 epimer) and glucosamine (2-amino-2-deoxy-D-glucose) are tested. Previous studies of wild-type abg have shown that it already displays small but measurable activity on PNP derivatives of D-mannose and even D-xylose, a 5-carbon sugar (Kempton & Withers, *Biochemistry* 31: 9961–9969, 1992). All of these sugars are custom synthesized to include various indolyl tags. Recently, it has also been found that enzymes such as abg can be used to synthesize novel oligosaccharides by manipulating their transglycosylase activities (Murata & Usui, Biosci. *Biotechnol. Biochem.* 61: 1059–1066, 1997).

The MicroColonyImager is used to engineer the ability to catalyze efficient hydrolysis or synthesis of unusual glycosides into abg, by isolating mutant abg whose properties of interest are altered compared to the wild type enzymes. The Y380F pseudo-wild type abg is evolved to catalyze efficient hydrolysis of unusual glycoside substrates, by using the method described in EXAMPLE 2, and substituting other chromogenic glycoside substrates for Red-gal.

This EXAMPLE opens up a potentially large arena for development of new enzymes for custom synthesis of oligosaccharides and other glycoside derivatives.

EXAMPLE 7

Application of MCI Screening Technology to Engineer Chiral Specificity in a Biocatalyst: Changing the Enantiomeric Excess (ee) of Rhizopus Lipase Esterases and lipases are used for chiral resolution of numerous chemicals that serve as basic building blocks in the production of pharmaceuticals, including carboxylic acids, alcohols, and amino acids. Although these enzymes hydrolyze a wide range of compounds, their stability and activity, as well as their stereoselectivity for a given substrate, are often insufficient for cost-effective manufacture of a desired pharmaceutical compound. Directed protein evolution can be used to change the properties of these biocatalysts so that they meet the economic and engineering requirements for chiral synthesis.

Many chromogenic and fluorogenic ester substrate analogs assaying able for assaying esterase and lipase activity. Products that precipitate upon hydrolysis (see, TABLES 1 and 2) are readily integrated into the solid phase assay format of the MicroColonyImager. Chromogenic derivatives containing a variety of indoxyl analogs as alcohol leaving groups, e.g., X-butyrate, Magenta-caprylate, Red-palmitate, produce colored precipitates and are commercially available, for example, from Biosynth International (Naperville, Ill.) or are readily synthesized. Esters containing 2-aryl substituted 4-(3H)-quinazolinone as the alcohol leaving group produce an insoluble fluorescent precipitate upon hydrolysis, and are commercially available from Molecular Probes (Eugene, Oreg.) or are readily synthesized. A sensitive solid phase fluorescence assay for lipases utilizing fatty acid interactions with rhodamine B has been described by Kouker & Jaeger (*App. Environ. Microbiol.* 53: 211–213, 1987). A novel dual-wavelength FRET assay using fluorogenic glycerolipid compounds containing pyrene or pyrylene as the fluorophore and a trinitrophenylamino residue as the quencher to measure both lipase activity and stereoselectivity has also recently been reported by Zandonella et al. (*J. Molecular Catalysis B: Enzymatic* 3: 127–130, 1997).

The lipase from *Rhizopus delemar* has been extensively studied and is available commercially, for example, from Sigma-Aldrich Corporation (St. Louis, Mo.). This enzyme has been cloned, sequenced, and expressed in *E. coli*. It has also been crystallized, and its structure has been detennined. Expression of the active prolipase form of this enzyme in *E. coli* allows large numbers of lipase mutants to be screened using solid phase assays. Using an *E. coli* expression system for the *Rhizopus delemar* lipase, site-directed mutagenesis has been used to alter the acyl binding site to improve its specificity for short- or medium-chain length fatty acids. The *Rhizopus delemar* lipase has been used in ester hydrolysis to produce alcohol substrates of high enantiomeric purities (>95% ee), which were subsequently used in the synthesis of optically active carbocyclic nucleosides (Tanaka et al., *J. Org. Chem.* 61: 6952–6957 1996).

Wild-type Rhizopus lipase displays poor enantioselectivity (15% ee residual ester) when it is used to hydrolyze 4-(benzoylamino)-2-cyclopentenecarboxylic acid methyl ester (Mahmoudian et al., *Enzyme Microb. Technol.* 14: 911–916, 1992). Carboxylic acid enantiomers with different chromogenic tags [1R,4S-4-(benzoylamino)-2-cyclopentenecarboxylic acid 5-bromo-4-chloro-3-indolyl ester and 1S,4R-4-(benzoylamino)-2-cyclopentenecarboxylic acid 6-chloro-3-indolyl ester] can be synthesized and used as substrates for an enantiomeric excess assay for *Rhizopus delemar* lipase. Cleavage of these esters results in the release of the indoxyl tag and the formation of an insoluble indigo derivative. The intensity of each color can be used to quantitate the amount of hydrolysis of each enantiomer.

Mutant forms of abg with altered substrate specificities were isolated by using two epimers (glucose and galactose) labeled with different chromogenic tags (see, EXAMPLE 2). The MicroColonyImager was able to identify color differences that reflected a change in the relative rates of cleavage of the two substrates. By labeling two enantiomers with different chromogenic tags, the solid phase MicroColonyImager system can be used to screen libraries of lipase mutants to identify mutants with increased enantiomeric excess (ee) values for a specific substrate. This is done by using multispectral analysis to identify color differences among microcolonies. Spectral differences correspond to differences in the relative rates of hydrolysis for the two derivatized enantiomers.

Error-prone PCR is used to generate libraries of point mutants in the prolipase gene. These libraries are screened using the MicroColonyImager to identify microcolonies whose spectra show the desired ratio of intensities in their absorption peaks, in order to identify mutants with improved ee. Ester substrates in which the indolyl tags are switched (e.g., in which the 6-chloro-3-indolyl tag is linked to the 1R,4S acid enantiomer and the 5-bromo-4-chloro-3-indolyl tag is linked to the 1S,4R acid enantiomer) are used in alternating rounds of mutagenesis. This eliminates any unwanted enzymes whose apparent increase in selectivity is based solely on differences in the indoxyl tags. Cycles of mutagenesis and screening are performed on the best mutants from each round of mutagenesis until there is no further increase in activity.

The improved lipase variants are used to hydrolyze untagged substrates (e.g., the methyl esters of the chiral acids), and the reaction products are characterized by chiral HPLC or capillary electrophoresis to determine the change in ee for each lipase variant. Enzymes with enhanced enantioselectivity can be used to improve the resolution of racemic mixtures of ester derivatives. These assays validate the use of the MicroColonyImager and solid phase screening assays for engineering the enantioselectivity of esterases and lipases, two classes of enzymes important for the synthesis of single-isomer pharmaceuticals.

EXAMPLE 8

Demonstration of Fluorescence Detection in Solid Phase; Evolving a Restriction Endonulease with Novel Specificity Hydrolases that utilize high molecular weight substrates play important roles in biochemistry, biotechnology and medicinal chemistry. A number of different in vitro assays have been developed to study these enzymes, but they encounter serious problems when applied to intact cells expressing the enzyme of interest. Membrane permeability problems inherent to high molecular weight compounds make it extremely difficult, for example, to screen bacterial libraries with peptides or oligonucleotides unless the enzyme is secreted or the cells are permeabilized or lysed. In the past, this type of assay has been performed on purified proteins in a fluorimeter (or in a microplate format), which limits the overall throughput for screening. The MicroColonyImager can be used to isolate hydrolase mutants that require high molecular weight substrates.

The restriction endonucleases are examples of a class of hydrolytic enzymes that cleave oligomeric substrates (in this case, duplex DNA) with a very high degree of specificity. One of the best-characterized endonucleases is EcoRI, a type II homodimeric enzyme from *E. coli* that has a subunit molecular weight of 31 kilodaltons (kDa). This enzyme recognizes the palindromic nucleotide sequence -GAATTC- and cleaves after the G. The protein has been crystallized, and the three-dimensional structure has been determined at a resolution of 2.7 Å. Site-directed mutagenesis has also determined the residues that are responsible for substrate specificity and phosphate bond cleavage. The amino acid sequence shows similarity to other restriction enzymes that possess identical or similar specificities, including ApoI, an enzyme from *Arthrobacter protophormiae* that cleaves the 4-fold degenerate nucleotide sequence -PuAATTPy-. (As used herein, Pu=purine; Py=pyrimidine.) Using this information as a starting point, the EcoRI gene in a cloned plasmid is mutagenized (using error-prone PCR) and used to screen the mutagenized library for mutants with significantly enhanced ability to cleave the -PuAATTPy-sequence, using an *E. coli* strain with an expression plasmid containing the EcoRI endonuclease and the required methylase genes.

Figure 7:
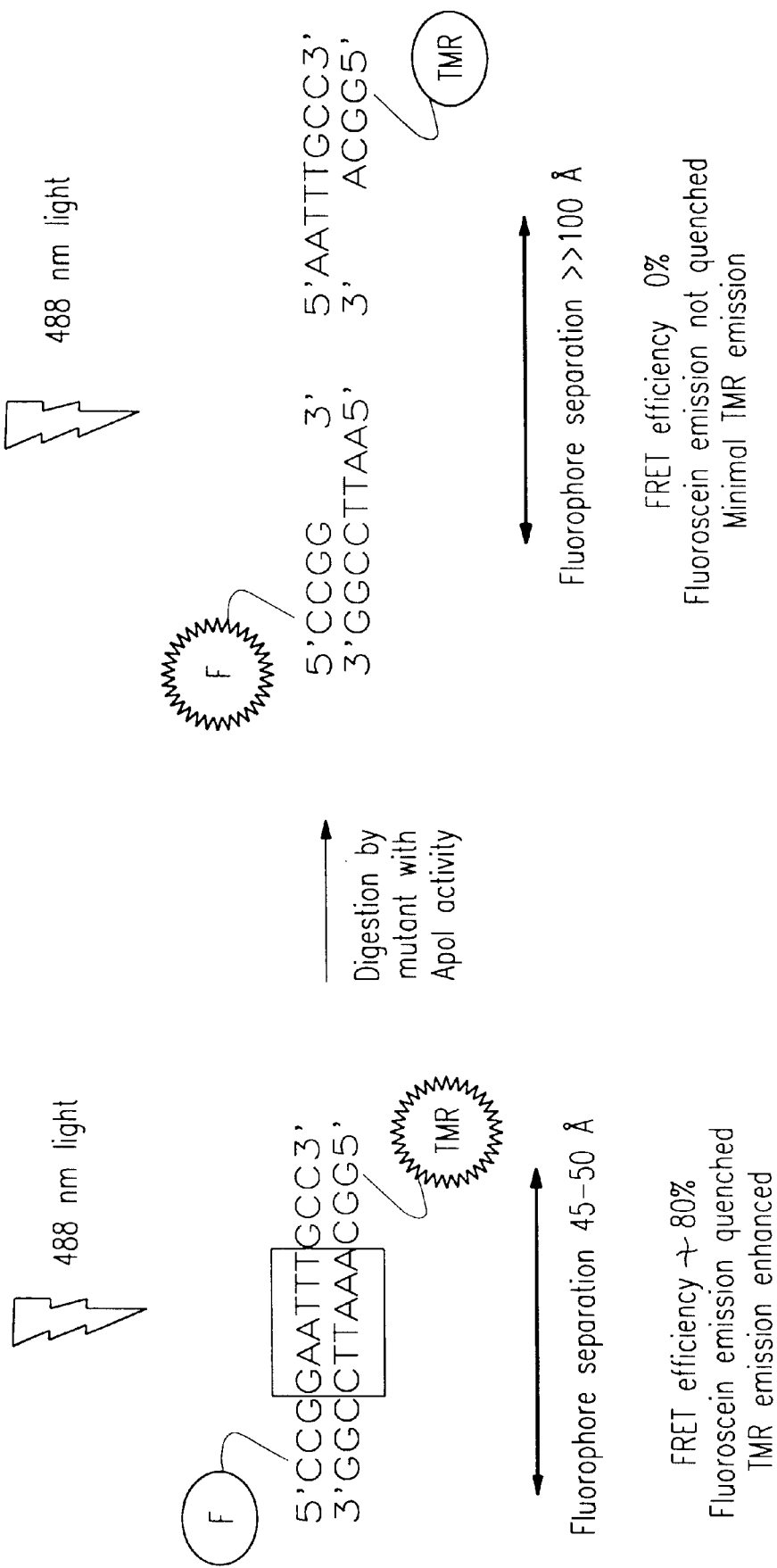
FIG. 7 is a schematic of the fluorescence resonance energy transfer (FRET)-based assay for identifying altered restriction enzyme specificity using the MicroColonyImager.

To screen for the novel activity, the fluorescence capability of the MicroColonyImager is used in an assay that is based on FRET (FIG. 7). FIG. 7 is a schematic of the fluorescence resonance energy transfer (FRET)-based assay for identifying altered restriction enzyme specificity using the MicroColonyImager. Colonies expressing mutagenized EcoRI enzyme are exposed to one of four substrates containing an ApoI recognition site. The dodecamer substrate contains fluorescein and tetramethylrhodamine (TMR) on its opposing 5'-termini. In the intact substrate, excitation of the donor (fluorescein) at 488 nm causes approximately 80% of the excitation energy to be re-emitted by the acceptor (TMR) at 580 nm. After the substrate is cleaved, the two fluorophores separate beyond the distance at which energy transfer is efficient, and hence 488 nm excitation results in only 510 nm emission by the donor, fluorescein.

To screen for mutants showing activity in the presence of one or more of the four possible ApoI recognition sequences, *E. coli* libraries containing the cloned EcoRi gene that has been mutagenized by error-prone PCR are created as described above. The mutated gene is transformed into an *E. coli* host along with genes for the ApoI and EcoRI methylases, so that the host genomic DNA and the introduced plasmid are not destroyed. Disks containing several thousand microcolonies are then lysed and treated with substrate solution. Fluorescence spectral images at time=0 establish the maximum FRET signal level, after which time microcolonies having a significant number of pixels that display a progressively decreasing FRET signal are candidates for evolving ApoI activity. The mutagenized library is screened against the four FRET substrates individually. In a separate set of experiments, the substrate containing the EcoRI recognition site serves as a positive control for the assay. In addition, if non-specific nuclease activity creates a measurable background signal, a fifth, non-recognized sequence is used to assay for this activity. If substrate/product diffusion is a problem, commercially available alkylated fluorescein and tetramethylrhodamine (TMR) is incorporated into the substrates. The substrate molecules consist of double-stranded 5'-labeled DNA that is non-palindromic, so that two single-stranded chains can be annealed together without forming homoduplexes. The two fluorophores in the FRET duplexes are separated by approximately 45–50 Å, a distance at which the FRET efficiency is approximately 80%. When the mutated enzyme successfully cleaves the substrate, the FRET efficiency drops to zero, and at the same time, the fluorescence emission of the donor fluorophore is completely restored. Measurement of these two signals by the MicroColonyImager indicates which clones are evolving ApoI activity. Mutants can be screened without using the optional GFP tag, but different dye pairs that do not overlap with GFP, such as the CyDye series, commercially available from Amersham Pharmacia Biotech Ltd. (Malvern, Pa.) can alternatively be used. Alternatively, BFP (a blue-shifted mutant of GFP that absorbs at 380 nm) could be used. A solid phase FRET assay can also be employed to evolve other commercially important oligomer-cleaving enzymes, such as proteases.

EXAMPLE 9

Use of the MicroColonyImager for Metabolic Engineering with Chromogenic Substrates that do not Employ Tags This EXAMPLE demonstrates that the MicroColonyImager can be used to image enzymatic reactions that generate colored or fluorescent products without using chromogenic (e.g., indolyl) or fluorogenic (e.g., fluorescein) tags. It also demonstrates that the MicroColonyImager can be used to detect the kinetics of natural product synthesis and improve the production of such molecules.

Cultured cells, microorganisms and consortia of microorganims (such as biofilms) frequently produce a desired biological molecule via complex biosynthetic pathways involving multiple enzyme activities. Occasionally, these pathways may even compete with one another for processing a given precursor that they have in common. Thus, to manipulate the synthetic reactions starting from the simple precursor, the products of at least two enzymes must be assayed to identify genetic variants that have the desired final output. Likewise, the relative flux through each of the pathways may need to be measured and possibly diverted. One example of this type of enzyme engineering is known as "metabolic" engineering (see, Cameron & Chaplen, *Curr. Opin. Biotechnol.* 8: 175–180, 1997). This technique has been widely used to modify metabolites, to produce new biosynthetic compounds, and to improve the performance of cultured cells.

In this EXAMPLE, the crtE, crtB, and crtI genes from Erwinia uredovora in yeast (*Candida utilis*) are expressed according to the method of Miura et al. (*Biotechnol. Bioeng.* 58: 306–308, 1998). These genes encode the synthase and desaturase enzymes that convert the common isoprenoid metabolite farnesyl pyrophosphate (FPP) into the carotenoid pigment lycopene. Lycopene is useful as a food colorant, nutritional supplement, and potential cancer preventative. Expression of this gene cluster has two effects on the host organism. (1) The cells synthesize lycopene, which is not produced by the wild-type *C. utilis* strain. Lycopene can be optically assayed because it has electronic absorption bands in the visible region at 445, 472, and 505 nm. Carotenoid fluorescence can also be monitored by exciting the sample at approximately 488 nm. (2) The cells reduce their production of ergosterol, which is normally synthesized from FPP, because the isoprenoid precursor is diverted to carotenoid synthesis.

The MicroColonyImager is used in either the absorption or fluorescence mode to directly monitor lycopene formation. The level of lycopene formation indicates how much of the isoprenoid carbon flux is being diverted away from the ergosterol pathway. Mutagenesis of the crt genes (or the genes for competing pathways) is used in combination with the MicroColonyImager assay to enhance the synthesis of lycopene and reduce the synthesis of other products as desired, as well as to change the enzymatic reactions that determine the chemical structure of the final carotenoid product (e.g., through regioselective modifications). Flux through the desired path is therefore maximized, and flux through the undesired path is reduced.

The method is carried out in the following steps:
1. Clone the crtE, crtB and crtI genes from Erwinia uredovora into a plasmid.
2. Sequentially subject each of these three genes to error-prone mutagenesis and insert the mutated genes to an expression plasmid.
3. Transform the expression plasmid into yeast.
4. Induce expression of the plasmid-encoded genes.
5. Assay the yeast using the MicroColonyImager to find those cells displaying enhanced kinetics for lycopene formation, as indicated by the characteristic absorption spectrum for this compound.
6. Further assay candidate microcolonies using the MicroColonyimager to find those cells displaying enhanced kinetics for lycopene formation, as indicated by the characteristic fluorescence spectrum for this compound (with excitation at 488 nm).
7. Optionally, subject the entire yeast genome to chemical mutagenesis in order to diminish the production of ergosterol.
8. Assay the effects of Step 7 by repeating Steps 5 and 6.
9. If the desired level of enhanced lycopene synthesis has been obtained, then End; otherwise, repeat Steps 2 through 8.

This EXAMPLE uses endogenous metabolites to generate the optical signal substrate. The color reaction is initiated by chemically inducing the expression of the cloned enzyme genes. This EXAMPLE does not limit the use of the MicroColonyImager for metabolic engineering with chromogenic substrates that do not employ tags, but rather shows one method for enhanced lycopene synthesis.

Although the invention has been described with reference to the presently preferred embodiment, it should be understood that various modifications can be made without departing from the spirit of the invention. Accordingly, the invention is limited only by the following claims.

What is claimed:

1. A method for imaging and analyzing microcolonies of cells, including the steps of:
   (a) forming in excess of 100 regions, each region including at least one biological cell on a substantially continuous base at an average density of at least about 10 regions per square centimeter;
   (b) initiating a chemical reaction in such regions that results in an optically detectable signal that changes over time;
   (c) automatically optically monitoring each region over time for changes in the optical signal of portions of such regions; and
   (d) indicating which of such portions have a desired change in optical signal.

2. The method of claim 1, wherein the step of automatically optically monitoring each region further includes the step of imaging the regions with a camera.

3. The method of claim 2, wherein the camera forms a pixel image of the regions and each region spans at least one pixel.

4. The method of claim 1, wherein the average density of regions on the base is at least about 200 regions per square centimeter.

5. The method of claim 1, wherein the step of automatically optically monitoring each region over time for changes in the optical signal of portions of such regions comprises acquiring and sorting single pixel data.

6. The method of claim 1, wherein the step of indicating includes the step of color-coding an image of the regions to indicate which of such portions have a desired change in optical signal.

7. The method of claim 1, further including the step of isolating samples from the portions having the desired change in optical signal.

8. The method of claim 7, wherein the step of isolating samples from the portions having the desired change in optical signal is performed automatically.

9. The method of claim 7, wherein the step of isolating samples from the portions having the desired change in optical signal is performed manually.

10. A method of performing solid-phase directed evolution enzyme screening, including the steps of:
    (a) generating an average density of at least 10 microcolonies of cells per square centimeter on a solid phase, wherein a plurality of microcolonies express variants of at least one enzyme;
    (b) contacting the expressed variants with at least one optical signal substrate, each indicative of a desired enzymatic activity; and
    (c) automatically detecting changes over time in one or more optical signals generated by one or more optical signal substrates in the microcolonies, wherein such changes indicate desired enzymatic activity of the variants of the enzyme.

11. The method of claim 10, wherein the step of detecting changes over time in one or more optical signals generated by one or more optical signal substrates in the microcolonies further comprises:
    indicating which microcolonies display change over time in such optical signal, wherein the desired change over time indicates desired enzymatic activity of the variants of the enzyme in the corresponding microcolonies.

12. The method of claim 10, wherein the step of contacting expressed variants includes the step of lysing the cells of the microcolonies sufficient to expose the expressed variants for contacting.

13. The method of claim 10, wherein the step of contacting expressed variants includes the step of permeabilizing the cells of the microcolonies sufficient to expose the expressed variants for contacting.

14. The method of claim 10, wherein the step of generating a density of at least 10 microcolonies of cells per square centimeter on a solid phase comprises:
    (a) generating a library of mutant cells on a solid phase, a plurality of such cells expressing variants of at least one enzyme, sufficient to generate an average density of at least 10 microcolonies of cells per square centimeter; and (b) inducing gene expression in the cells sufficient to express such variants.

15. The method of claim 14, wherein the induction of gene expression comprises: induction of a virus-encoded gene.

16. The method of claim 15, wherein the virus is a lytic virus.

17. The method of claim 15, wherein the virus is a temperate virus.

18. The method of claim 14, further comprising:

(a) inducing mutagenesis of DNA encoding at least one enzyme; and (b) transforming the DNA into biological cells to make a library of mutant cells, a plurality of such cells expressing variants of the enzyme.

19. The method of claim 11, further including the step of: obtaining a sample of an indicated microcolony.

20. The method of claim 19, wherein the sample is obtained automatically.

21. The method of claim 19, wherein the sample is obtained manually.

22. The method of claim 18, further including the steps of:

(a) obtaining DNA from the samples; and (b) transforming the DNA into biological cells.

23. The method of claim 10, further including the step of: measuring enzymatic parameters for the variants of the enzyme.

24. The method of claim 10, wherein the optical signal substrate is colored as a reactant or a product.

25. The method of claims 10, wherein the optical signal substrate is at least one selected from the group consisting of a chromogenic substrate, fluorogenic substrate, fluorescence resonance energy transfer substrate, or chemiluminescent substrate.

26. The method of claims 10, wherein the enzyme is selected from at least one selected from the group consisting of a hydrolytic enzyme, a protease, an esterase, a glycosidase, an isomerase, a lyase, a polymerase, a synthase, a synthetase, a monooxygenase, a dioxygenase, a transferase, and an oxido-reductase.

27. The method of claims 10, wherein the desired enzymatic activity is at least one selected from a change in enantiomeric excess of a reaction, substrate specificity of a reaction, stereospecificity of a reaction, rate of a reaction, regiospecificity of a reaction, thermostability of an enzyme, or stability of an enzyme in the presence of specified chemicals.

28. The method of claims 10, wherein the enzyme is a GFP-enzyme fusion protein.

29. A method of performing solid-phase enzyme discovery screening, including the steps of:

(a) generating a density of at least 10 microcolonies of cells per square centimeter on a solid phase, wherein a plurality of microcolonies consist of cells containing members of a recombinant DNA library;

(b) contacting the microcolonies with at least one optical signal substrate, each indicative of a desired enzymatic activity; and (c) automatically detecting changes over time in one or more optical signals generated by one or more optical signal substrates in the microcolonies, wherein such changes indicate desired enzymatic activity.

30. The method of claim 29, wherein the step of automatically detecting changes over time in one or more optical signals generated by one or more optical signal substrates in the microcolonies further comprises:

indicating which microcolonies display change over time in such optical signals, wherein the change over time indicates desired enzymatic activity in the corresponding microcolonies.

31. The method of claim 29, wherein the step of contacting the microcolonies includes the step of lysing the cells of the microcolonies sufficient to expose enzymes in the microcolonies for contacting.

32. The method of claim 29, wherein the step of contacting the microcolonies includes the step of permeabilizing the cells of the microcolonies sufficient to expose enzymes in the microcolonies for contacting.

33. The method of claim 29, wherein the step of generating a density of at least 10 microcolonies of cells per square centimeter on a solid phase further comprises:

inducing gene expression in the cells sufficient to express proteins encoded by members of the recombinant DNA library.

34. The method of claim 33, wherein the induction of gene expression comprises:

induction of a virus-encoded gene.

35. The method of claim 34, wherein the virus is a lytic virus.

36. The method of claim 34, wherein the virus is a temperate virus.

37. The method of claim 29, further including the step of: obtaining a sample of an indicated microcolony.

38. The method of claim 37, wherein the sample is obtained automatically.

39. The method of claim 37, wherein the sample is obtained manually.

40. The method of claim 37, further including the steps of:

(a) obtaining DNA from the samples; and (b) transforming the DNA into biological cells.

41. The method of claim 30, further including the step of: measuring enzymatic parameters for enzyme expressed by the indicated microcolony.

42. The method of claims 29, wherein the optical signal substrate is colored as a reactant or a product.

43. The method of claims 29, wherein the optical signal substrate is selected from the group consisting of a chromogenic substrate, fluorogenic substrate, fluorescence resonance energy transfer substrate, or chemiluminescent substrate.

44. The method of claims 29, wherein the desired enzymatic activity is selected from at least one of the group consisting of a hydrolytic enzyme, a protease, an esterase, a glycosidase, an isomerase, a lyase, a polymerase, a synthase, a synthetase, a monooxygenase, a dioxygenase, a transferase, and an oxido-reductase.

45. The method of claims 29, wherein the desired enzymatic activity is selected from at least one of a change in enantiomeric excess of a reaction, substrate specificity of a reaction, stereo specificity of a reaction, rate of a reaction, regiospecificity of a reaction, thermostability of an enzyme, or stability of an enzyme in the presence of specified chemicals.

46. An instrument for imaging and analyzing microcolonies of cells on a target, including:

(a) a light source for controllably emitting light having a selected set of wavelengths;

(b) a camera for controllably imaging light received from the target within a selected set of wavelengths;

(c) a sampling mechanism for controllably selecting samples from the target;

(d) a processor, coupled to the light source, the camera, and the sampling mechanism, for controlling the wavelengths of light emitted from the light source, the wavelengths of light imaged by the camera, and operation of the sampling mechanism; wherein the instrument automatically images regions of the target over time for changes in rate in any optical signal of portions of such regions, and automatically indicates which of such portions have a desired change over time in optical signal.

47. The instrument of claim 46, wherein the instrument further comprises:

an integrating chamber interposed between the light source and the target for dispersing the emitted light to uniformly illuminate the target.

48. The instrument of claim 46, wherein the instrument further comprises:

a fiber optic illuminator.

49. The instrument of claim 46, wherein the instrument automatically selects a sample with the sampling mechanism from at least one indicated portion.

50. The instrument of claim 46, wherein the light source includes a variable filter for controlling the wavelengths of light emitted by the light source.

* * * * *